(12) United States Patent
Vincent

(10) Patent No.: US 12,234,459 B2
(45) Date of Patent: Feb. 25, 2025

(54) METHODS OF TREATING CANCER AND/OR ENHANCING SENSITIVITY TO CANCER TREATMENT BY INCREASING TUMOR MUTATION BURDEN OR TUMOR INDELS

(71) Applicant: Mark David Vincent, London (CA)

(72) Inventor: Mark David Vincent, London (CA)

(73) Assignee: Mark David Vincent, London (CA)

( * ) Notice: Subject to any disclaimer, the term of this patent is extended or adjusted under 35 U.S.C. 154(b) by 306 days.

(21) Appl. No.: 16/757,583

(22) PCT Filed: Oct. 23, 2018

(86) PCT No.: PCT/CA2018/051341
§ 371 (c)(1),
(2) Date: Apr. 20, 2020

(87) PCT Pub. No.: WO2019/079891
PCT Pub. Date: May 2, 2019

(65) Prior Publication Data
US 2021/0198675 A1  Jul. 1, 2021

Related U.S. Application Data

(60) Provisional application No. 62/646,543, filed on Mar. 22, 2018, provisional application No. 62/646,147, filed on Mar. 21, 2018, provisional application No. 62/580,570, filed on Nov. 2, 2017, provisional application No. 62/575,708, filed on Oct. 23, 2017.

(51) Int. Cl.
*C12N 15/113* (2010.01)
*A61K 31/7105* (2006.01)
*A61K 39/395* (2006.01)
*A61P 35/00* (2006.01)

(52) U.S. Cl.
CPC ...... *C12N 15/1137* (2013.01); *A61K 31/7105* (2013.01); *A61K 39/3955* (2013.01); *A61P 35/00* (2018.01); *C12N 2310/11* (2013.01); *C12N 2310/341* (2013.01); *C12N 2320/31* (2013.01)

(58) Field of Classification Search
CPC .............. C12N 15/1137; C12N 15/113; C12N 2310/11; C12N 2310/341; A61P 35/00; A61P 35/02; A61P 35/04
See application file for complete search history.

(56) References Cited

U.S. PATENT DOCUMENTS 5,646,267 A * 7/1997 Stec ............... C07F 9/6578
                                              536/25.1

FOREIGN PATENT DOCUMENTS

| WO | WO-0129262 A2 * | 4/2001 | ........ C12Q 1/6876 |
|---|---|---|---|
| WO | WO/2002/010364 A2 | 2/2002 | |
| WO | WO-03072732 A2 * | 9/2003 | ........ C07K 14/47 |
| WO | WO/2008/066624 | 6/2008 | |
| WO | WO2008066624 A2 | 6/2008 | |
| WO | WO-2009027641 A2 * | 3/2009 | ........ A61K 31/519 |
| WO | WO2012122645 A1 | 9/2012 | |
| WO | WO 2015/171918 A2 | 11/2015 | |
| WO | WO/2017/106964 A1 | 6/2017 | |
| WO | WO2017182783 A2 | 10/2017 | |

OTHER PUBLICATIONS

Campesato et al (Oncotarget, 2015, vol. 6, pp. 34221-34227). (Year: 2015).*
Liontos et al (Ann Transl Med, 2016, vol. 4, 6 pages) (Year: 2016).*
The abstract of Koo et al (Cancer Research, 2019, vol. 79, No. 13, Abstract No. 861) (Year: 2019).*
Zhang et al (Molecular therapy—Nucleic Acids, 2015, vol. 4, e264, 8 pages) (Year: 2015).*
Sameer et al (European Journal of Cancer Prevention, 2014, vol. 23, pp. 246-257) (Year: 2014).*
Yoshida et al (European Journal of Human Genetics, 2011, vol. 19, pp. 320-325). (Year: 2011).*
Westdorp et al (Cancer Immunol Immunother, 2016, vol. 65, pp. 1249-1259) (Year: 2016).*
Kamola et al, (Nucleci Acids Research, 2015, vol. 43, pp. 8638-8650) (Year: 2015).*
Hocke, S. et al.: "A synthetic lethal screen identifies ATR-inhibition as a novel therapeutic approach for POLD1-deficient cancers", Oncotarget, vol. 7, No. 6, Feb. 9, 2016 (Feb. 9, 2016), pp. 7080-7095, XP055549975, DOI: doi: 10.18632/oncotarget.6857.
Rizvi, N.A. et al.: "Mutational landscape determines sensitivity to PD-1 blockade in non-small cell lung cancer", Science, vol. 348, No. 6230, Apr. 3, 2015 (Apr. 3, 2015), pp. 124-128, XP055566207, ISSN: 1095-9203, DOI: doi: 10.1126/science.aaa1348.
Santin, A.D. et al.: "Regression of Chemotherapy-Resistant Polymerase epsilon (POLE) Ultra-Mutated and MSH6 Hyper-Mutated Endometrial Tumors with Nivolumab", Clinical Cancer Research, vol. 22, No. 23, Dec. 1, 2016 (Dec. 1, 2016), pp. 5682-5687, XP055594120, ISSN: 1078-0432.

(Continued)

*Primary Examiner* — Karen A. Canella
(74) *Attorney, Agent, or Firm* — Antoinette G Giugliano; Antoinette G Giugliano PC

(57) ABSTRACT

Methods of treating cancer or enhancing sensitivity to cancer therapies, including immunotherapies by increasing tumor mutation burden, are provided. The methods use therapeutics directed against DNA polymerase proofreading and/or mismatch repair enzymes such as MLH1, MSH2, MSH6 or PMS2. The therapeutics can be used alone, in tandem or in combination with other cancer therapies, in particular with immunotherapies. Also provided are antisense therapeutics targeting DNA polymerase proofreading and/or mismatch repair enzymes.

8 Claims, 15 Drawing Sheets

Specification includes a Sequence Listing.

(56) References Cited

OTHER PUBLICATIONS

German O, G et al.: "Inactivation of DNA repair triggers neoantigen generation and impairs tumour growth", Nature, vol. 552, No. 7683, Dec. 7, 2017 (Dec. 7, 2017), pp. 116-120, XP055594122, ISSN: 1476-4687.
Written Opinion of PCT Application No. PCT/CA2018/051341 mailed, Feb. 19, 2019.
International Search Report of PCT Application No. PCT/CA2018/051341, mailed, Feb. 19, 2019.
European Search Report of EP Application No. 18869815.3, mailed Nov. 4, 2020.
Kent W. Mouw et al: "DNA Damage and Repair Biomarkers of Immunotherapy Response". Cancer Discovery. vol. 7. No. 7. pp. 675-693 Jul. 5, 2017 (Jul. 5, 2017).
Dharam P Chauhan et al: "Advances in Brief Antisense Inhibition of hMLH1 Is Not Sufficient for Loss of DNA Mismatch Repair Function in the HCT116?Chromosome 3 Cell Line 1" Clinical Cancer Research. vol. 6. pp. 3827-3831 Oct. 1, 2000 (Oct. 1, 2000).
Mateusz Rytelewski et al: "Reci procal positive selection for weakness preventing olaparib resistance by inhibiting BRCA2". Oncotarget. vol. 7. No. 15. 12 pp. 20825-20839 Apr. 2016 (Apr. 12, 2016).
A Fedler et al: "Increased sensitivity of p53-deficient cells to anticancer agents due to loss of Pms2". British Journal of Cancer. vo 1 • 87. No. 9. 21 pp. 1027-1033 Oct. 2002 (Oct. 21, 2002).
Chabanon, R., et al., "Mutational Landscape and Sensitivity to Immune Checkpoint Blockers", *Clinical Cancer Research*, 22(17), pp. 4309-4321, Aug. 31, 2016 (Aug. 31, 2016).
Canadian Examination Report for Application No. 3,079,907, dated Oct. 28, 2024 (5 pages).

* cited by examiner

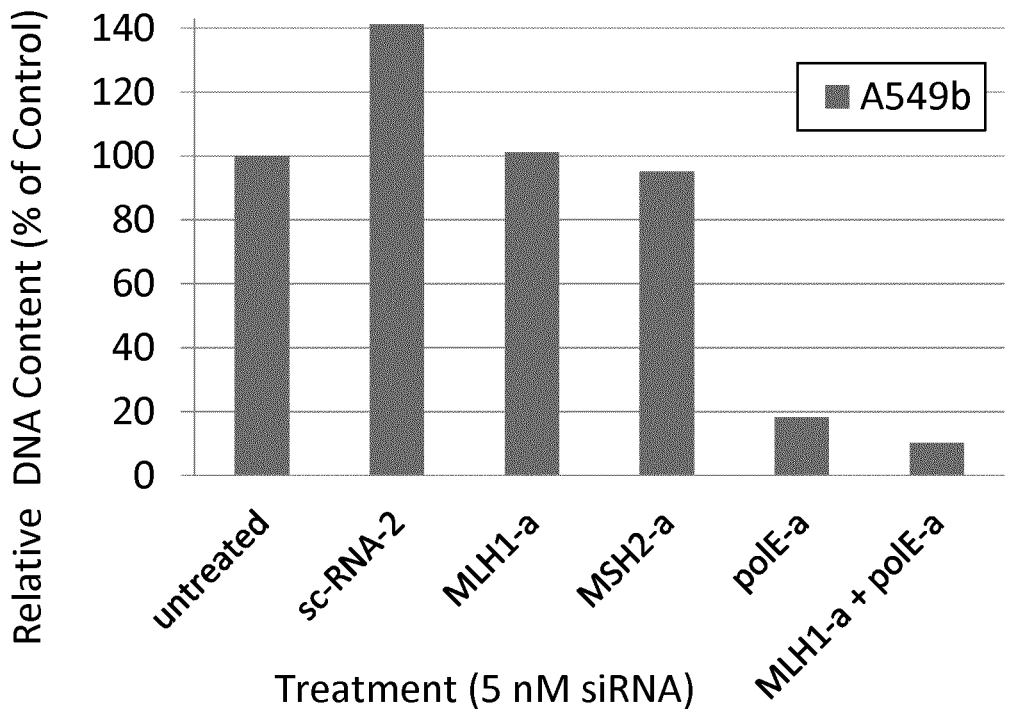
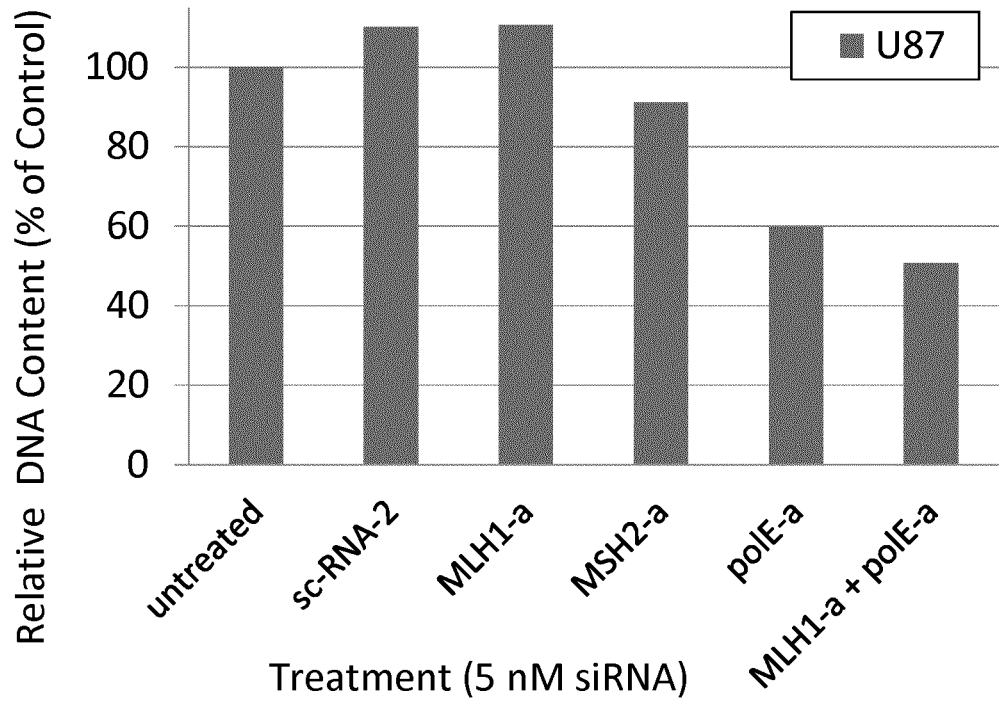
Figure 4

| ASO ID | $IC_{50}$ (nM) | $IC_{80}$ (nM) | max. KD |
|---|---|---|---|
| X43368 | 0.087 | 0.791 | 85.5% |
| X43369 | 0.859 | 4.755 | 88.8% |
| X43370 | 0.393 | 2.310 | 87.9% |
| X43371 | 0.057 | 0.387 | 91.4% |
| X43372 | 0.258 | 1.014 | 87.5% |
| X43380** | 0.038 | 0.404 | 88.5% |
| X43395 | 0.077 | 0.757 | 89.8% |
| X43408** | 0.034 | 0.136 | 90.3% |
| X43409 | 0.190 | 1.699 | 87.2% |
| X43410 | 0.052 | 0.951 | 89.3% |
| X43411 | 0.067 | 0.845 | 88.4% |
| X43412 | 0.336 | 1.809 | 90.9% |
| X43413 | 0.078 | 0.926 | 87.0% |
| X43414 | 0.085 | 0.508 | 90.5% |
| X43415** | 0.032 | 0.180 | 88.0% |
| X43423*** | 0.403 | 1.727 | 92.2% |
| X43425 | 0.934 | 11.093 | 82.6% |
| X43442 | 0.517 | 2.697 | 91.2% |

**best LNA ASO
***best MOE ASO

Figure 5b

U87 Glioblastoma cell TMB

| Target gene | conc | Sequence alterations | Insertions | Deletions | SNV's | Total NSV's | TMB (mt/Mb) | Comment |
|---|---|---|---|---|---|---|---|---|
| None | 5nM | 52 | 964 | 1211 | 37603 | 21787 | 573 | Scrambled siRNA control |
| MLH1 | 5nM | 62 | 996 | 1211 | 37489 | 21628 | 569 | Effect of The siRNA MLH1-a |
| MLH1-a vs scram | | +10 | +32 | 0 | -114 | -159 | -4 | Effect of siRNA MLH1-a confined to increased insertions |
| MSH2 | 5nM | 64 | 1022 | 1242 | 37533 | 21764 | 573 | Effect of the siRNA MSH2-a |
| MSH2-a vs scram | | +12 | +58 | +31 | -70 | -23 | -1 | Large increase in indels |
| POLE | 5nM | 59 | 1010 | 1259 | 37551 | 21694 | 571 | Effect of the siRNA POLE-a |
| POLE-a vs scram | | +7 | +46 | +48 | -52 | -93 | -2 | Large increase in indels due to the siRNA POLE-a |
| MLH1 and POLE | 5nM + 5nM | 63 | 1019 | 1218 | 37319 | 21592 | 568 | Effect of the combination of the siRNA's POLE-a and MLH1-a |
| MLH1-a and POLE-s vs scram | | +11 | +55 | +7 | -284 | -195 | -5 | Large increase in insertions |

Figure 6a

A549 lung cancer cell TMB

| Target gene | conc | Sequence alterations | Insertions | Deletions | SNV's | Total NSV's | TMB (mt/Mb) | Comment |
|---|---|---|---|---|---|---|---|---|
| None | 5nM | 64 | 946 | 1192 | 37663 | 22205 | 584 | Scrambled siRNA control |
| MLH1 | 5nM | 89 | 1013 | 1236 | 38443 | 22633 | 596 | Effect of the siRNA MLH1-a |
| MLH1-a vs scram | | +25 | +67 | +44 | +780 | +429 | +11 | Incremental effect of ↓MLH1 over scrambled control |
| MSH2 | 5nM | 72 | 977 | 1196 | 37977 | 22363 | 589 | Effect of the siRNA MSH2-a |
| MSH2-a vs scram | | +8 | +31 | +4 | +314 | +158 | +4 | Incremental effect of ↓MSH2 over scrambled control |
| POLE | 5nM | 70 | 966 | 1251 | 37930 | 22481 | 591 | Effect of the siRNA POLE-a |
| POLE-a vs scram | | +6 | +20 | +59 | +267 | +276 | +7 | Incremental effect of ↓POLE over scrambled control |
| MLH1 and POLE | 5nM + 5nM | 66 | 939 | 1183 | 37777 | 22380 | 589 | Effect of the combination of ↓MLH1 and ↓POLE |
| MLH1-a and POLE-a Vs scram | | +2 | -7 | -9 | +114 | +175 | +5 | Incremental effect of combined↓MLH1 and ↓POLE. (Less than each individually) |

Figure 6b

SK-Mel-5 melanoma TMB

| Gene | Conc | Sequence alteration | Insertions | Deletions | SNV's | Total NSV's | TMB mt/Mb | comment |
|---|---|---|---|---|---|---|---|---|
| None | 5nM | 52 | 906 | 1095 | 37765 | 21820 | 574 | Scrambled siRNA control |
| MLH1 | 5nM | 42 | 929 | 1168 | 37705 | 21874 | 576 | |
| ↓MLH1 | | -10 | +23 | +71 | -60 | +54 | +2 | Large increase in indels due to ↓MLH1 |
| MSH2 | 5nM | 47 | 918 | 1139 | 37522 | 21675 | 570 | |
| ↓MSH2 | | -5 | +12 | +42 | -243 | -145 | -5 | Increase in indels due to siRNA to MSH2, despite fewer SNVs (antiproliferativeactivity) |
| POLE | 5nM | 43 | 918 | 1121 | 38490 | 22315 | 587 | |
| ↓POLE | | -9 | +12 | +17 | +785 | +495 | +13 | Increase in indels and SNV's due to siRNA to POLE leads to a large increase in TMB |
| MLH1 and POLE | 5nM + 5nM | 40 | 854 | 1062 | 37706 | 21814 | 574 | |
| ↓MLH1 and ↓POLE | | -12 | -52 | -33 | -59 | -6 | 0 | Fewer mutations because this combination of siRNA to MLH1 and siRNA to POLE is very antiproliferative |

Figure 6c

HT-29 colon cancer cell TMB

| Target gene | Conc | Sequence alterations | Insertions | Deletions | SNV's | Total NSVs | TMB Mut/Mb | Comment |
|---|---|---|---|---|---|---|---|---|
| None; scrambled control | 10nM | 79 | 1028 | 1352 | 39576 | 22673 | 504 | Scrambled control at 10nM conc |
| MLH1 | 5nM | 76 | 1039 | 1327 | 41974 | 22791 | 507 | Due to siRNA to MLH1 |
| ↓MLH1 vs scrambled | | +4 | +13 | -17 | +2500 | +118 | +3 | Large increase in NSV's. Mild increase in insertions |
| MSH6 | 5nM | 76 | 1025 | 1291 | 39382 | 22641 | 503 | Due to siRNA against MSH6 |
| ↓MSH6 vs scrambled | | +4 | -1 | -53 | -92 | -77 | -2 | Appears to be ineffective |
| PMS2 | 5nM | 77 | 1101 | 1378 | 39905 | 22971 | 511 | Due to siRNA against PMS2 (PMS2-c seq id) |
| ↓PMS2 vs scrambled | | +5 | +75 | +34 | +431 | +253 | +6 | Large increase in SNV's as well as indels |
| POLD1 | 5nM | 78 | 1044 | 1330 | 39697 | 22760 | 506 | Due to siRNA against POLD1 (POLD-b) |
| ↓POLD1 vs scrambled | | +6 | +18 | -14 | +86 | +223 | +1 | Mild increase in insertions; large increase in SNV's and NSVs |
| POLE | 5nM | 72 | 1050 | 1343 | 39553 | 22680 | 504 | Due to siRNA against POLE |
| ↓POLE vs scrambled | | 0 | +24 | -1 | +79 | -28 | -1 | Modest increase in insertions and SNV's |
| PMS2 +POLE combined | 5nM + 5nM | 75 | 1044 | 1291 | 39530 | 22647 | 503 | |
| ↓PMS2 + ↓POLE vs scrambled | | -4 | +16 | -1161 | -46 | -26 | -1 | Mild increase in insertions |
| POLD1 and POLE combined | 5nM + 5nM | 80 | 1069 | 1364 | 39649 | 22809 | 507 | Due to the combination of siRNA's to POLD1 (POLD-b) and POLE (POLE-a') |
| ↓POLD1 and ↓POLE vs scrambled | | +1 | +41 | +12 | +73 | +136 | +3 | Moderate increase in insertions, mild increase in deletions, and moderate increase in SNV's and total NSV's |

Figure 6d

| ASO ID | Type | SEQ ID No. | Gapmer Sequence | MSH2 | | | |
|---|---|---|---|---|---|---|---|
| | | | | 25 nM mean | 25 nM SD | 5 nM mean | 5 nM SD |
| X43415 | LNA | 31 | AbsTtsAtsj5MdCjs5MdCjs5MdCjbdTtsdGsdAsdTsdA.sdGsdAsdGbsTbsCbsGb | 0.045 | 0.010 | 0.093 | 0.010 |
| X43412 | LNA | 32 | GbsTbsCbsdGsdGsdTsdTsdAsdAsdGsdTs5MdCjsdTbsGbsTbsGb | 0.049 | 0.022 | 0.108 | 0.016 |
| X43410 | LNA | 33 | AbsTbsCbsdGsdAs[5MdC]sdGsdAsdAsdGsdAsdTbsCbsTb | 0.050 | 0.020 | 0.110 | 0.013 |
| X43411 | LNA | 34 | GbsGbsGbsdAsdAsdTs[5MdC]sdGsdAs[5MdC]sdGsdAsdAsGbsTbsAbsAb | 0.050 | 0.025 | 0.120 | 0.008 |
| X43414 | LNA | 35 | TbsAbsCbs[5MdC]s[5MdC]sdTsdAsdAsdGsdAsdGsdAsdTsdA.sdGsTbsCbsGbsGb | 0.051 | 0.013 | 0.103 | 0.021 |
| X43423 | MOE | 36 | GmsAmsCmsCmsAmsdTs[5MdC]sdAsdAsdAs[5MdC]sdTsdGs[5MdC]sdAsdGsAmsCmsAmsUmsUm | 0.055 | 0.017 | 0.101 | 0.015 |
| X43409 | LNA | 37 | TbsTbsGbsdAs[5MdC]sdGsdAsdGsdTsdAsdAsdAsTbsCbsTb | 0.062 | 0.028 | 0.118 | 0.021 |
| X43413 | LNA | 38 | AbsAbsGbsdTs[5MdC]sdGsdsAsdTsdAsdAsdGsdAsdTsdCbsTbsGb | 0.065 | 0.013 | 0.097 | 0.013 |
| X43395 | LNA | 39 | CbsTbsCbsdTsdGsdAsdTsdA.sdGsdsAsdGsdTsCbsGbsGbsTb | 0.072 | 0.008 | 0.088 | 0.032 |
| X43370 | LNA | 40 | GbsGbsGbsdTsdAsdAsdTs[5MdC]sdGsdAsdAsGbsTbsCb | 0.072 | 0.011 | 0.143 | 0.016 |
| X43371 | LNA | 41 | GbsTbsCbsdGsdGsdTsdTsdGsdAsdGsdAsdTsdCbsTbsGb | 0.074 | 0.024 | 0.108 | 0.044 |
| X43369 | LNA | 42 | AbsTbsGbsdAsGbsdGsdAsdAsdGsdAsdGsdAsdTsdAbsAbsTb | 0.074 | 0.014 | 0.179 | 0.028 |
| X43406 | LNA | 43 | CbsTbsCbsdTsdAsdGsdAs[5MdC]sdTsdGs[5MdC]sdAs[5MdC]sdGsA.bs.AbsCbsGb | 0.075 | 0.023 | 0.062 | 0.028 |
| X43368 | LNA | 44 | TbsCbsGbsdAs[5MdC]sdGsdGsdAsdAsdGsGsdTsdAsAbsAbsTbsCb | 0.077 | 0.022 | 0.152 | 0.016 |
| X43372 | LNA | 45 | AbsGbsTbsdA.s[5MdC]sdGsdGsdTsdTsdAsdGsdAsbsTbsCbsTb | 0.077 | 0.012 | 0.140 | 0.019 |
| X43425 | MOE | 46 | CmsCmsGmsCmsUmsdTs[5MdC]sdTsdGsdGs[5MdC]sdAsdGsdAsAmsUmsAmsAmsAm | 0.080 | 0.007 | 0.195 | 0.037 |
| X43442 | MOE | 47 | AmsAmsAmsUmsUmsdTs[5MdC]sdTsdGsdGs[5MdC]sdAsdGsdAsdGsUmsCmsGmsGmsUm | 0.080 | 0.019 | 0.087 | 0.031 |
| X43380 | LNA | 48 | GbsTbsAbsdTsdAs[5MdC]sdGsdAsdTsdAbsAbsGbsGb | 0.080 | 0.014 | 0.120 | 0.013 | dR: DNA residues (including 5-methyl-C)
Nb: LNA residues (LNA-A, LNA-5-methyl-C, LNA-G, LNA-T)
Nm: 2'MOE residues (including 5-methyl-C including 2'MOE-C and 2'MOE-T)
s: phosphorothioate
*potentially toxic

Figure 7

| ASO ID | Type | SEQ ID No. | Gapmer Sequence | MSH2 | | | |
|---|---|---|---|---|---|---|---|
| | | | | 25 nM mean | 25 nM SD | 5 nM mean | 5 nM SD |
| X48374 | LNA | 49 | GbsCbsAbsAbdAsdTsdTs[5MdC]sdGsdGsdTsdTsAbsAbsGbsAb | 0.082 | 0.035 | 0.093 | 0.017 |
| X48391 | LNA | 50 | TbsCbsTbsdGsdGsdGsdAsdAsdTs[5MdC]sdGsdAsdCbsGbsAbsAb | 0.083 | 0.007 | 0.110 | 0.033 |
| X48354 | LNA | 51 | TbsGbsAbsdTsdAsdGsdAsdAsdGsdTs[5MdC]sdAsdGsTbsAbsAbsCb | 0.083 | 0.031 | 0.124 | 0.009 |
| X48367 | LNA | 52 | CbsGbsAbs[5MdC]sdGsdAsAsdGsdTsdAsdAsAbsTbsCbsTb | 0.083 | 0.002 | 0.242 | 0.040 |
| X48424 | MOE | 53 | UmsAmsGmsCmsCmsAmsdAsdTs[5MdC]sdAsdAsdAs[5MdC]sdTsdGs[5MdC]sdGsdGsmsAmsCmsAmsUm | 0.084 | 0.008 | 0.152 | 0.017 |
| X48392 | LNA | 54 | GbsTbsCbsdGsdGsdTsdTsdGsdTsdTsdAsAbsCbsTbsGbsAb | 0.086 | 0.017 | 0.107 | 0.033 |
| X48373 | LNA | 55 | CbsAbsAbsdTs[5MdC]s[5MdC]sdTsdGsdAsdTsdTsdAsAbsAbsAbsTb | 0.087 | 0.018 | 0.209 | 0.031 |
| X48396 | LNA | 56 | TbsAbsCbs[5MdC]s[5MdC]sdTsdGsdAsdAsdGsdGsdAsAbsTbsCbsGb | 0.088 | 0.019 | 0.105 | 0.012 |
| X48368 | LNA | 57 | TbsCbsGbsdAs[5MdC]sdGsdAsdAsdAs[5MdC]sdAsdAsAbsTbsCbsTb | 0.088 | 0.023 | 0.096 | 0.020 |
| X48375 | LNA | 58 | GbsAbsGbsdTs[5MdC]sdGsdGsdGsdTsdAsdAsdAs[5MdC]sAbsAbsTbsCb | 0.089 | 0.029 | 0.114 | 0.018 |
| X48441 | MOE | 59 | UmsAmsGmsCmsAmsAmsGmsdTs[5MdC]sdGsdGsdTsdTsdAsdAsGmsAmsUmsCmsUm | 0.089 | 0.019 | 0.086 | 0.031 |
| X48443 | MOE | 60 | UmsAmsAmsGmsAmsGmsdTs[5MdC]sdGsdGsdTsdAsdAs[5MdC]sdAsdAsUmsCmsUmsUmsGm | 0.090 | 0.025 | 0.114 | 0.020 |
| X48393 | LNA | 62 | CbsAbsAbsdTsdGsdTsdAsdGs[5MdC]sdGsdTsdGsdTsdTsAbsGsbsGbsAb | 0.091 | 0.028 | 0.106 | 0.026 |
| X48397 | LNA | 63 | GbsTbsAbsdTs[5MdC]sdGsdTs[5MdC]sdAsdGsdTsdTsAbsGsbsAb | 0.092 | 0.015 | 0.124 | 0.017 |
| X48444 | MOE | 64 | AmsAmsCmsAmsUmsmsdAsdAsdTsdAsdGs[5MdC]sdGsdTsdGsdTs[5MdC]sdGsAbsAbsAmsAmsCm | 0.097 | 0.022 | 0.156 | 0.017 |
| X48390 | LNA | 65 | TbsGbsBbsdGsdAsdAsdTs[5MdC]sdGsdGsdTs[5MdC]sdGsdAsdAbsAbsGbsTb | 0.098 | 0.008 | 0.106 | 0.065 |
| X48437 | MOE | 65 | CmsGmsGmsmsUmsdUmsdTsdAsdAsdGsdAsdTs[5MdC]sdGsdGsdTs[5MdC]sGsAmsAmsCmsAm | 0.098 | 0.015 | 0.154 | 0.055 |
| X48438 | MOE | 66 | UmsCmsAmsGmsUmsdUmsdTsdAsdAsdGsdAsdTs[5MdC]sdGsdGsAmsAmsCmsAm | 0.099 | 0.018 | 0.161 | | dM: DNA residues (including 5methyl-C)
Nb: LNA residues (LNA-A, LNA-5-methyl-C, LNA-G, LNA-T)
Nm: 2'MOE residues (including 5methyl-2'MOE-C and 2'MOE-T)
s: phosphorothioate
*: potentially toxic

Figure 7 continued

| ASO ID | Type | SEQ ID No. | Gapmer Sequence | MSH2 25 nM mean | 25 nM SD | 5 nM mean | 5 nM SD |
|---|---|---|---|---|---|---|---|
| X43448 | MOE | 67 | UmsAmsGmsUmsUmsdGsdAsdTsdTsdTsdAs[5M-dC]sdTsdAs[5M-dC]s[5M-dC]sdTsdCsmsUmsGmsAmsUm | 0.100 | 0.033 | 0.324 | 0.029 |
| X43436 | MOE | 68 | UmsAmsAmsGmsAmsdTs[5M-dC]sdTsdGsdGsdAsdTs[5M-dC]sdAsdAsdAsmsCmsGmsAm | 0.108 | 0.020 | 0.161 | 0.042 |
| X43445 | MOE | 69 | UmsAmsCmsCmsAmsdCmsdTsdGsdAsdTsdAsdGsdAsdGsdAsdTsdTs[5M-dC]sdAsdTsmsGmsAmsAm | 0.106 | 0.032 | 0.294 | 0.041 |
| X43447 | MOE | 70 | UmsAmsUmsGmsAmsCmsdTs[5M-dC]sdGsdTsdAsdGsdAsdGsdAsdGsdAsdTsdTsmsCmsGmsGm | 0.109 | 0.024 | 0.173 | 0.021 |
| X43382 | LNA | 71 | TbsAbsCbsdTs[5M-dC]sdGsdGs[5M-dC]sdGsdTsdAs[5M-dC]sdAsdTsdAsAsGbsAbsTb | 0.109 | 0.024 | 0.586 | 0.047 |
| X43377 | LNA | 72 | TbsGbsGbsdTbs[5M-dC]sdTsdAs[5M-dC]sdGsdTsdAs[5M-dC]sdAsdTsdAsTbsAbsTb | 0.109 | 0.027 | 0.198 | 0.014 |
| X43376 | LNA | 73 | GbsGbsTbs[5M-dC]sdGsdTsdAs[5M-dC]sdAsdTsdAsTsdAsTbsGbsAbsTb | 0.125 | 0.019 | 0.142 | 0.022 |
| X43378 | LNA | 74 | GbsCbsTbsdGsdGs[5M-dC]sdGsdTs[5M-dC]sdTsdAs[5M-dC]sdAsdTsdAsTb | 0.125 | 0.025 | 0.205 | 0.027 |
| X43289 | LNA | 75 | AbsTbsCbsdGsdAgs[5M-dC]sdGsdAsdGsdAsAsAbsTbsCb | 0.128 | 0.018 | 0.103 | 0.026 |
| X43446 | MOE | 76 | AmsUmsAmsCmsCmsAmsdCmsdTsdGsdTsdAsdGsdTsdCmsGmsCmsAm | 0.132 | 0.027 | 0.221 | 0.043 |
| X43452 | MOE | 77 | AmsUmsCmsGmsAmsUmsdAs[5M-dC]sdGsdAsdTsdAsdGsdAsdGmsUmsCmsCm | 0.133 | 0.026 | 0.528 | 0.066 |
| X43450 | MOE | 78 | UmsCmsGmsAmsUmsa[5M-dC]sdGsdTsdAsdGsdAsdTsdAs[5M-dC]sdAsdAmsCmsGm | 0.137 | 0.015 | 0.672 | 0.050 |
| X43435 | MOE | 79 | GmsAmsAmsUmsCmsdGs[5M-dC]sdGsdTsdAsdGsdAsdTsdAsdAsmsAmsGmsUm | 0.144 | 0.011 | 0.144 | 0.031 |
| X43420 | MOE | 80 | CmsAmsGmsAmsCmsdAsdTsdAsdTsdTsdAs[5M-dC]sdTsdAsdAs[5M-dC]sdTsUmsCmsUmsGm | 0.149 | 0.042 | 0.233 | 0.059 |
| X43462 | MOE | 81 | AmsUmsCmsGmsAmsUmsdAs[5M-dC]sdGsdAsdGsdAsAsmsAmsCmsUm | 0.156 | 0.040 | 0.792 | 0.053 |
| X43457 | MOE | 82 | UmsAmsCmsGmsAmsUmsdAsmsdCmsdGsdAsdTsdAsdGsdAsGsdTs[5M-dC]sGmsCmsUmsCm | 0.157 | 0.026 | 0.445 | 0.044 |
| X43459 | MOE | 83 | CmsCmsAmsUmsdCmsdGsdAsdTsdAsdGsdAsdTsdAsGsdAsGmsUmsCmsCm | 0.159 | 0.027 | 0.527 | 0.034 |
| X43439 | MOE | 84 | GmsCmsAmsGmsAmsdGsdTs[5M-dC]sdGsdGsdAsdGsdAsUsmsCmsUmsGmsAm | 0.160 | 0.019 | 0.135 | 0.045 | dN: DNA residues (including 5-methyl-C)
Nb: LNA residues (LNA-A, LNA-5-methyl-C, LNA-G, LNA-T)
Nm: 2'MOE residues (including 5-methyl 2'MOE-C and 2'MOE-T)
s: phosphorothioate
*potentially toxic

| ASO ID | Type | SEQ ID No. | Gapmer Sequence | MSH2 | | | |
|---|---|---|---|---|---|---|---|
| | | | | 25 nM mean | 25 nM SD | 5 nM mean | 5 nM SD |
| X43440 | MOE | 103 | GmsGmsCmsAmsAmsdGsdTsdTsdGsdGsdTsdAsdAsdGsAmsUmsCmsUmsGm | 0.226 | 0.022 | 0.151 | 0.035 |
| X43449 | MOE | 104 | UmsGmsGmsAmsUmsdTsdGsdGsdTsdTsdAs(5MdC)sdTsdTsdAs(5MdC)sdAsdTsdGsAmsGmsCmsGm | 0.230 | 0.033 | 0.332 | 0.029 |
| X43452 | MOE | 105 | CmsCmsAmsAmsUmsdTsdTsdGsdGsdGs(5MdC)s(5MdC)sdGsdAsdTsdGsAmsGmsUmsAmsCm | 0.231 | 0.057 | 0.661 | 0.026 |
| X43452 | MOE | 106 | AmsAmsUmsCmsAmsdAsdTsdAs(5MdC)sdGsdAsdAsdAs(5MdC)sdTsdAsdAsdAmsUmsCmsCm | 0.232 | 0.020 | 0.425 | 0.114 |
| X43455 | MOE | 107 | GmsCmsCmsCmsdTsdTsdGsdAsdGsdTs(5MdC)sdAs(5MdC)sdTsAmsAmsGmsAmsUm | 0.240 | 0.028 | 0.904 | 0.067 |
| X43396* | LNA | 108 | CbsGbsGbsdTsdTsdGsdAsdGsdGsdTs(5MdC)sdGsdAs(5MdC)sdTsdGsdAbsTb | 0.249 | 0.083 | 0.092 | 0.012 |
| X43555* | LNA | 109 | AbsAbsAbsdTsdGs(5MdC)sdGs(5MdC)sdGsdAs(5MdC)sdGsdAs(5MdC)scbsCbsCbsAb | 0.251 | 0.059 | 0.589 | 0.088 |
| X43433 | LNA | 110 | GmsGmsAmsAmsdTs(5MdC)s(5MdC)sdGsdAs(5MdC)sdTsdAscbsCbsdTsdAsAmsAmsdUmsCmsUm | 0.272 | 0.046 | 0.342 | 0.035 |
| X43398* | LNA | 111 | CbsAbsCbs(5MdC)s(5MdC)sdGsdAsdGsdAsdAs(5MdC)sdTsdTsdGsTbsGbsGbsAb | 0.276 | 0.097 | 0.193 | 0.050 |
| X43454 | MOE | 112 | CmsUmsAms(5MdC)smsUms(5MdC)sdGsdGsdGsdAs(5MdC)sdAsdAsdGsdAsdAsUmsGmsAmsGm | 0.286 | 0.044 | 0.844 | 0.076 |
| X43385 | LNA | 113 | TbsGbsAbsdTsdAsdGsdAsdGsdAs(5MdC)s(5MdC)sdTsGs(5MdC)s(5MdC)sGbsCbsAb | 0.289 | 0.017 | 0.517 | 0.053 |
| X43405* | LNA | 114 | AbsAbsAbsdAsdTs(5MdC)sdGs(5MdC)sdGsdAs(5MdC)sdAs(5MdC)sGsAbsCbsAbsTbsAb | 0.305 | 0.026 | 0.498 | 0.030 |
| X43379* | LNA | 115 | GbsGbsCbsdTsdGsdAsdGs(5MdC)sdGsdAs(5MdC)sdGsdAs(5MdC)s(5MdC)scbsCbsCbsAb | 0.314 | 0.059 | 0.174 | 0.027 |
| X43405 | LNA | 116 | GbsGbsAbsdTsdGsdAsdGs(5MdC)sdGsdAs(5MdC)sdGsdAs(5MdC)sGsCbsCbsCbsCb | 0.326 | 0.043 | 0.477 | 0.093 |
| X43384* | LNA | 117 | AbsAbsAbsdAsdTs(5MdC)sdGs(5MdC)sdGsdAs(5MdC)sdAs(5MdC)sGsAbsCbsAbsTbsAb | 0.326 | 0.038 | 0.537 | 0.034 |
| X43422 | MOE | 118 | GmsUmsUmsGmsAmsdTsdGsdGsdGsdAsdTs(5MdC)sdGsdAs(5MdC)sGsAmsCmsAmsUm | 0.377 | 0.059 | 0.571 | 0.110 |
| X43428 | MOE | 119 | AmsAmsUmsAmsAmsdTs(5MdC)sdTsdTsdAs(5MdC)sdGsdAsdAs(5MdC)sdTsdGsAmsAmsAm | 0.429 | 0.026 | 0.219 | 0.070 |
| X43417 | MOE | 120 | GmsAmsAmsAmsAmsdGs(5MdC)s(5MdC)sdGsdGsdAs(5MdC)sdGsGs(5MdC)s(5MdC)sAmsCmsAmsCm | 0.442 | 0.026 | 0.675 | 0.040 |
| X43399 | LNA | 121 | GbsCbsCbs(5MdC)s(5MdC)s(5MdC)sdTsdAs(5MdC)sdTsdGsdAs(5MdC)s(5MdC)sdTsdAs(5MdC)sGbsCbsTbsAb | 0.635 | 0.060 | 0.987 | 0.031 |
| X43418 | MOE | 122 | AmsGmsAmsAmsAmsmGmsdGs(5MdC)s(5MdC)sdGsdGsdAs(5MdC)sdGsGs(5MdC)s(5MdC)sAmsCmsAmsCm | 0.672 | 0.297 | 0.723 | 0.056 |
| X43419 | MOE | 123 | GmsAmsAmsAmsAmsdGs(5MdC)s(5MdC)sdGsdGsdAs(5MdC)sdGsGs(5MdC)sdGsAmsCmsAmsAm | 0.697 | 0.125 | 0.625 | 0.128 |
| X43421 | MOE | 124 | UmsGmsAmsAmsmAmsmdGs(5MdC)sdGsdGsdGsdAs(5MdC)sdGsdGs(5MdC)s(5MdC)sAmsGmsCmsAm | 0.824 | 0.313 | 0.649 | 0.035 |
| X43420 | MOE | 125 | UmsGmsAmsGmsCmsdTsdAs(5MdC)sdGsdGsdGsdAs(5MdC)sdGsdGsGs(5MdC)s(5MdC)sAmsGmsCmsCm | 0.843 | 0.248 | 0.899 | 0.088 |
| X43453 | MOE | 126 | CmsGmsGmsGmsCmsdTsdAsdAsdAs(5MdC)sdGsdAsdGsGsdTsdGs(5MdC)s(5MdC)sAmsCmsAmsCm | 0.943 | 0.052 | 1.058 | 0.046 | dN: DNA residues (including 5meCyt-C)
Nt: LNA residues (LNA-A, LNA-5-methyl-C, LNA-G, LNA-T)
Nm: 2'MOE residues (including 5-methyl-2'MOE-C and 2'MOE-T)
s: phosphorothioate
*potentially toxic

Figure 7 continued

```
                        SEQUENCE LISTING

<160> NUMBER OF SEQ ID NOS: 144

<210> SEQ ID NO 1
<211> LENGTH: 19
<212> TYPE: RNA
<213> ORGANISM: Artificial Sequence
<220> FEATURE:
<223> OTHER INFORMATION: POLE ASO target sequence

<400> SEQUENCE: 1
gcgaggaaca ggcgaaaua                                                19

<210> SEQ ID NO 2
<211> LENGTH: 19
<212> TYPE: RNA
<213> ORGANISM: Artificial Sequence
<220> FEATURE:
<223> OTHER INFORMATION: POLE ASO target sequence

<400> SEQUENCE: 2
ggaggagggu gcuucguau                                                19

<210> SEQ ID NO 3
<211> LENGTH: 19
<212> TYPE: RNA
<213> ORGANISM: Artificial Sequence
<220> FEATURE:
<223> OTHER INFORMATION: POLE ASO target sequence

<400> SEQUENCE: 3
ggacaggcgu uacgaguuc                                                19

<210> SEQ ID NO 4
<211> LENGTH: 19
<212> TYPE: RNA
<213> ORGANISM: Artificial Sequence
<220> FEATURE:
<223> OTHER INFORMATION: POLE ASO target sequence

<400> SEQUENCE: 4
```

```
cucggaagcu ggaagauua                                             19
```

<210> SEQ ID NO 5
<211> LENGTH: 20
<212> TYPE: RNA
<213> ORGANISM: Artificial Sequence
<220> FEATURE:
<223> OTHER INFORMATION: POLE ASO target sequence

<400> SEQUENCE: 5

```
ucacgcagug aaugcuuuuc                                            20
```

<210> SEQ ID NO 6
<211> LENGTH: 20
<212> TYPE: RNA
<213> ORGANISM: Artificial Sequence
<220> FEATURE:
<223> OTHER INFORMATION: POLE ASO target sequence

<400> SEQUENCE: 6

```
acagccucac aggagcaguu                                            20
```

<210> SEQ ID NO 7
<211> LENGTH: 20
<212> TYPE: RNA
<213> ORGANISM: Artificial Sequence
<220> FEATURE:
<223> OTHER INFORMATION: POLE ASO target sequence

<400> SEQUENCE: 7

```
acugaccacc cugacugucc                                            20
```

<210> SEQ ID NO 8
<211> LENGTH: 20
<212> TYPE: RNA
<213> ORGANISM: Artificial Sequence
<220> FEATURE:
<223> OTHER INFORMATION: POLE ASO target sequence

<400> SEQUENCE: 8

```
uuuucaggga gcucagacgu                                            20
```

<210> SEQ ID NO 9
<211> LENGTH: 19
<212> TYPE: RNA
<213> ORGANISM: Artificial Sequence
<220> FEATURE:
<223> OTHER INFORMATION: POLD1-a target sequence

<400> SEQUENCE: 9

```
aguuggagau ugaccauua                                             19
```

<210> SEQ ID NO 10
<211> LENGTH: 19
<212> TYPE: RNA
<213> ORGANISM: Artificial Sequence
<220> FEATURE:
<223> OTHER INFORMATION: POLD1-b

<400> SEQUENCE: 10

```
cgagagagca uguuugggu                                             19
```

<210> SEQ ID NO 11
<211> LENGTH: 19
<212> TYPE: RNA
<213> ORGANISM: Artificial Sequence

```
<220> FEATURE:
<223> OTHER INFORMATION: POLD1-c target sequence

<400> SEQUENCE: 11
gcaaaggcau cuucccuga                                                    19

<210> SEQ ID NO 12
<211> LENGTH: 19
<212> TYPE: RNA
<213> ORGANISM: Artificial Sequence
<220> FEATURE:
<223> OTHER INFORMATION: POLD1-d target sequence

<400> SEQUENCE: 12
gcacagaaac ugggccuga                                                    19

<210> SEQ ID NO 13
<211> LENGTH: 18
<212> TYPE: RNA
<213> ORGANISM: Artificial Sequence
<220> FEATURE:
<223> OTHER INFORMATION: POLD1-d target sequence

<400> SEQUENCE: 13
aggauggaag cgggaccc                                                     18

<210> SEQ ID NO 14
<211> LENGTH: 19
<212> TYPE: RNA
<213> ORGANISM: Artificial Sequence
<220> FEATURE:
<223> OTHER INFORMATION: MSH2-a target sequence

<400> SEQUENCE: 14
gcagaugaau agugcugua                                                    19

<210> SEQ ID NO 15
<211> LENGTH: 19
<212> TYPE: RNA
<213> ORGANISM: Artificial Sequence
<220> FEATURE:
<223> OTHER INFORMATION: MSH2-b target sequence

<400> SEQUENCE: 15
gaagagaccu uaacuaugc                                                    19

<210> SEQ ID NO 16
<211> LENGTH: 19
<212> TYPE: RNA
<213> ORGANISM: Artificial Sequence
<220> FEATURE:
<223> OTHER INFORMATION: MSH2-c target sequence

<400> SEQUENCE: 16
caacauauau ucgacaaac                                                    19

<210> SEQ ID NO 17
<211> LENGTH: 19
<212> TYPE: RNA
<213> ORGANISM: Artificial Sequence
<220> FEATURE:
<223> OTHER INFORMATION: MSH2-d target sequence

<400> SEQUENCE: 17
gagaaugauu gguauuugg                                                    19
```

```
<210> SEQ ID NO 18
<211> LENGTH: 19
<212> TYPE: RNA
<213> ORGANISM: Artificial Sequence
<220> FEATURE:
<223> OTHER INFORMATION: MLH1-a target sequence

<400> SEQUENCE: 18
ggaaguuguu ggcagguau                                                19

<210> SEQ ID NO 19
<211> LENGTH: 19
<212> TYPE: RNA
<213> ORGANISM: Artificial Sequence
<220> FEATURE:
<223> OTHER INFORMATION: MLH1-b target

<400> SEQUENCE: 19
ccagaugguu cguacagau                                                19

<210> SEQ ID NO 20
<211> LENGTH: 19
<212> TYPE: RNA
<213> ORGANISM: Artificial Sequence
<220> FEATURE:
<223> OTHER INFORMATION: MLH-c target

<400> SEQUENCE: 20
gaaguaguga uaaggucua                                                19

<210> SEQ ID NO 21
<211> LENGTH: 19
<212> TYPE: RNA
<213> ORGANISM: Artificial Sequence
<220> FEATURE:
<223> OTHER INFORMATION: MLH-d target

<400> SEQUENCE: 21
uaucuucauu cuucgacua                                                19

<210> SEQ ID NO 22
<211> LENGTH: 20
<212> TYPE: RNA
<213> ORGANISM: Artificial Sequence
<220> FEATURE:
<223> OTHER INFORMATION: MLH-e target

<400> SEQUENCE: 22
augcacugug ggauguguuc                                               20

<210> SEQ ID NO 23
<211> LENGTH: 19
<212> TYPE: RNA
<213> ORGANISM: Artificial Sequence
<220> FEATURE:
<223> OTHER INFORMATION: PMS2-a target

<400> SEQUENCE: 23
uaaugaagcu guucugaua                                                19

<210> SEQ ID NO 24
<211> LENGTH: 19
<212> TYPE: RNA
<213> ORGANISM: Artificial Sequence
<220> FEATURE:
<223> OTHER INFORMATION: PMS2-b target
```

```
<400> SEQUENCE: 24
ucuaugaguu cuuuagcua                                                  19

<210> SEQ ID NO 25
<211> LENGTH: 19
<212> TYPE: RNA
<213> ORGANISM: Artificial Sequence
<220> FEATURE:
<223> OTHER INFORMATION: PMS2-c target

<400> SEQUENCE: 25
ggauguugaa gguaacuua                                                  19

<210> SEQ ID NO 26
<211> LENGTH: 19
<212> TYPE: RNA
<213> ORGANISM: Artificial Sequence
<220> FEATURE:
<223> OTHER INFORMATION: PMS2-d target

<400> SEQUENCE: 26
ggaauauuaa gaaggagua                                                  19

<210> SEQ ID NO 27
<211> LENGTH: 19
<212> TYPE: RNA
<213> ORGANISM: Artificial Sequence
<220> FEATURE:
<223> OTHER INFORMATION: MSH-a target

<400> SEQUENCE: 27
cgaaguagcc gccaaauaa                                                  19

<210> SEQ ID NO 28
<211> LENGTH: 19
<212> TYPE: RNA
<213> ORGANISM: Artificial Sequence
<220> FEATURE:
<223> OTHER INFORMATION: MSH6-b target

<400> SEQUENCE: 28
ccacauggau gcucuuauu                                                  19

<210> SEQ ID NO 29
<211> LENGTH: 19
<212> TYPE: RNA
<213> ORGANISM: Artificial Sequence
<220> FEATURE:
<223> OTHER INFORMATION: MSH6-c target

<400> SEQUENCE: 29
gcagaagggc uauaaagua                                                  19

<210> SEQ ID NO 30
<211> LENGTH: 19
<212> TYPE: RNA
<213> ORGANISM: Artificial Sequence
<220> FEATURE:
<223> OTHER INFORMATION: MSH6-d target

<400> SEQUENCE: 30
gggccaagau ggaggguua                                                  19

<210> SEQ ID NO 31
```

```
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(6)
<223> OTHER INFORMATION: m5c

<400> SEQUENCE: 31
atannntgat agagtcg                                                    17

<210> SEQ ID NO 32
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (13)..(13)
<223> OTHER INFORMATION: m5c

<400> SEQUENCE: 32
gtcggttaag atntggg                                                    17

<210> SEQ ID NO 33
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 33
atcgangaag taaatct                                                    17

<210> SEQ ID NO 34
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(10)
<223> OTHER INFORMATION: m5c

<400> SEQUENCE: 34
gggaatngan gaagtaa                                                    17

<210> SEQ ID NO 35
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(6)
<223> OTHER INFORMATION: m5c

<400> SEQUENCE: 35
tacnntgata gagtcgg                                                    17
```

```
<210> SEQ ID NO 36
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(13)
<223> OTHER INFORMATION: m5c

<400> SEQUENCE: 36
ggccatnaan tgnggacauu                                               20

<210> SEQ ID NO 37
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(5)
<223> OTHER INFORMATION: m5c

<400> SEQUENCE: 37
tcgangaagt aaatctt                                                  17

<210> SEQ ID NO 38
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(5)
<223> OTHER INFORMATION: m5c

<400> SEQUENCE: 38
aagtnggtta agatctg                                                  17

<210> SEQ ID NO 39
<211> LENGTH: 16
<212> TYPE: DNA
<213> ORGANISM: Artificial Sequence
<220> FEATURE:
<223> OTHER INFORMATION: synthesized MSH2 gapmer sequence

<400> SEQUENCE: 39
ccctgataga gtcggt                                                   16

<210> SEQ ID NO 40
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(10)
<223> OTHER INFORMATION: m5c

<400> SEQUENCE: 40
gggaatngan gaagt                                                    15

<210> SEQ ID NO 41
<211> LENGTH: 15
<212> TYPE: DNA
```

```
<213> ORGANISM: Artificial Sequence
<220> FEATURE:
<223> OTHER INFORMATION: synthesized MSH2 gapmer sequence

<400> SEQUENCE: 41
gtcggttaag atctg                                                    15

<210> SEQ ID NO 42
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 42
atcgangaag taaat                                                    15

<210> SEQ ID NO 43
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(12)
<223> OTHER INFORMATION: m5c

<400> SEQUENCE: 43
ctctatantg angaacc                                                  17

<210> SEQ ID NO 44
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(5)
<223> OTHER INFORMATION: m5c

<400> SEQUENCE: 44
tcgangaagt aaatc                                                    15

<210> SEQ ID NO 45
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(4)
<223> OTHER INFORMATION: m5c

<400> SEQUENCE: 45
agtnggttaa gatct                                                    15

<210> SEQ ID NO 46
<211> LENGTH: 20
<212> TYPE: DNA
<213> ORGANISM: Artificial Sequence
<220> FEATURE:
<223> OTHER INFORMATION: synthesized MSH2 gapmer sequence
```

<220> FEATURE:
<221> NAME/KEY: misc_feature
<222> LOCATION: (12)..(13)
<223> OTHER INFORMATION: m5c

<400> SEQUENCE: 46
ccggutgagg tnntgauaaa                                          20

<210> SEQ ID NO 47
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(12)
<223> OTHER INFORMATION: m5c

<400> SEQUENCE: 47
aaacutnttg gnaagucggu                                          20

<210> SEQ ID NO 48
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(9)
<223> OTHER INFORMATION: m5c

<400> SEQUENCE: 48
gtatangtna ttagg                                               15

<210> SEQ ID NO 49
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(7)
<223> OTHER INFORMATION: n is a, c, g, or t

<400> SEQUENCE: 49
gcaagtnggt taaga                                               15

<210> SEQ ID NO 50
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (10)..(10)
<223> OTHER INFORMATION: m5c

<400> SEQUENCE: 50
tctgggaatn gacgaa                                              16

<210> SEQ ID NO 51
<211> LENGTH: 16
<212> TYPE: DNA
<213> ORGANISM: Artificial Sequence
<220> FEATURE:

```
<223> OTHER INFORMATION: synthesized MSH2 gapmer sequence
<220> FEATURE:
<221> NAME/KEY: misc_feature
<222> LOCATION: (10)..(10)
<223> OTHER INFORMATION: m5c

<400> SEQUENCE: 51
tgatagagtn ggtaac                                                       16

<210> SEQ ID NO 52
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(4)
<223> OTHER INFORMATION: m5c

<400> SEQUENCE: 52
cgangaagta aatct                                                        15

<210> SEQ ID NO 53
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(11)
<223> OTHER INFORMATION: m5c
<220> FEATURE:
<221> NAME/KEY: misc_feature
<222> LOCATION: (14)..(14)
<223> OTHER INFORMATION: n is a, c, g, t or u

<400> SEQUENCE: 53
uggccatnaa ntgnggacau                                                   20

<210> SEQ ID NO 54
<211> LENGTH: 16
<212> TYPE: DNA
<213> ORGANISM: Artificial Sequence
<220> FEATURE:
<223> OTHER INFORMATION: synthesized MSH2 gapmer sequence

<400> SEQUENCE: 54
gtcggttaag atctgg                                                       16

<210> SEQ ID NO 55
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 55
caagtnggtt aagat                                                        15

<210> SEQ ID NO 56
<211> LENGTH: 16
<212> TYPE: DNA
<213> ORGANISM: Artificial Sequence
```

```
<220> FEATURE:
<223> OTHER INFORMATION: synthesized MSH2 gapmer sequence
<220> FEATURE:
<221> NAME/KEY: misc_feature
<222> LOCATION: (4)..(5)
<223> OTHER INFORMATION: m5c

<400> SEQUENCE: 56
tacnntgata gagtcg                                                     16

<210> SEQ ID NO 57
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(5)
<223> OTHER INFORMATION: m5c

<400> SEQUENCE: 57
tcgangaagt aaatct                                                     16

<210> SEQ ID NO 58
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(11)
<223> OTHER INFORMATION: m5c

<400> SEQUENCE: 58
gagtnggtaa naatc                                                      15

<210> SEQ ID NO 59
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (9)..(9)
<223> OTHER INFORMATION: m5c

<400> SEQUENCE: 59
uggcaagtng gttaagaucu                                                 20

<210> SEQ ID NO 60
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(13)
<223> OTHER INFORMATION: m5c

<400> SEQUENCE: 60
uagagtnggt aanaaucuug                                                 20

<210> SEQ ID NO 61
<211> LENGTH: 16
<212> TYPE: DNA
```

```
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 61
caagtnggtt aagatc                                                     16

<210> SEQ ID NO 62
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: m5c

<400> SEQUENCE: 62
gtatangtna ttagga                                                     16

<210> SEQ ID NO 63
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (14)..(14)
<223> OTHER INFORMATION: m5c

<400> SEQUENCE: 63
acccugatag agtngguaac                                                 20

<210> SEQ ID NO 64
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(11)
<223> OTHER INFORMATION: m5c

<400> SEQUENCE: 64
tgggaatnga ngaagt                                                     16

<210> SEQ ID NO 65
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (11)..(11)
<223> OTHER INFORMATION: m5c

<400> SEQUENCE: 65
cgguuaagat ntgggaaucg                                                 20
```

<210> SEQ ID NO 66
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (12)..(12)
<223> OTHER INFORMATION: m5c

<400> SEQUENCE: 66
ucggutaaga tntgggaauc                                               20

<210> SEQ ID NO 67
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (14)..(15)
<223> OTHER INFORMATION: m5c

<400> SEQUENCE: 67
uaguugattt atanncugau                                               20

<210> SEQ ID NO 68
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(15)
<223> OTHER INFORMATION: m5c

<400> SEQUENCE: 68
uaagatntgg gaatngacga                                               20

<210> SEQ ID NO 69
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (15)..(15)
<223> OTHER INFORMATION: m5c

<400> SEQUENCE: 69
uaccctgata gagtngguaa                                               20

<210> SEQ ID NO 70
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(7)
<223> OTHER INFORMATION: m5c

<400> SEQUENCE: 70

| uauacnntga tagagucggu | 20 |

<210> SEQ ID NO 71
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(9)
<223> OTHER INFORMATION: m5c

<400> SEQUENCE: 71

| tactngggnt aagat | 15 |

<210> SEQ ID NO 72
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(9)
<223> OTHER INFORMATION: m5c

<400> SEQUENCE: 72

| tggtngtana tatgg | 15 |

<210> SEQ ID NO 73
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(8)
<223> OTHER INFORMATION: m5c

<400> SEQUENCE: 73

| ggtngtanat atgga | 15 |

<210> SEQ ID NO 74
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(11)
<223> OTHER INFORMATION: m5c

<400> SEQUENCE: 74

| gctggtngta natat | 15 |

<210> SEQ ID NO 75
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 75

```
atcgangaag taaatc                                                    16

<210> SEQ ID NO 76
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m6c

<400> SEQUENCE: 76
auaccntgat agagtcggua                                                20

<210> SEQ ID NO 77
<211> LENGTH: 20
<212> TYPE: DNA
<213> ORGANISM: Artificial Sequence
<220> FEATURE:
<223> OTHER INFORMATION: synthesized MSH2 gapmer sequence

<400> SEQUENCE: 77
aucguaggta gaagtuccuc                                                20

<210> SEQ ID NO 78
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 78
uccaungtag gtagaaguuc                                                20

<210> SEQ ID NO 79
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (12)..(15)
<223> OTHER INFORMATION: m5c

<400> SEQUENCE: 79 gaucuggaa tngangaagu                                                 20

<210> SEQ ID NO 80
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (14)..(14)
<223> OTHER INFORMATION: m5c

<400> SEQUENCE: 80
cgacgaagta aatntucuug                                                20
```

<210> SEQ ID NO 81
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(7)
<223> OTHER INFORMATION: m5c

<400> SEQUENCE: 81
auccatngta ggtagaaguu                                           20

<210> SEQ ID NO 82
<211> LENGTH: 20
<212> TYPE: DNA
<213> ORGANISM: Artificial Sequence
<220> FEATURE:
<223> OTHER INFORMATION: synthesized MSH2 gapmer sequence

<400> SEQUENCE: 82
ucguaggtag aaguuccucu                                           20

<210> SEQ ID NO 83
<211> LENGTH: 20
<212> TYPE: DNA
<213> ORGANISM: Artificial Sequence
<220> FEATURE:
<223> OTHER INFORMATION: synthesized MSH2 gapmer sequence

<400> SEQUENCE: 83
ccaucgtagg tagaaguucc                                           20

<210> SEQ ID NO 84
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(7)
<223> OTHER INFORMATION: m5c

<400> SEQUENCE: 84
gcaagtnggt taagaucugg                                           20

<210> SEQ ID NO 85
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (14)..(15)
<223> OTHER INFORMATION: m5c

<400> SEQUENCE: 85
aaccggttga ggtnnugaua                                           20

<210> SEQ ID NO 86
<211> LENGTH: 20
<212> TYPE: DNA
<213> ORGANISM: Artificial Sequence
<220> FEATURE:
<223> OTHER INFORMATION: synthesized MSH2 gapmer sequence -continued

```
<220> FEATURE:
<221> NAME/KEY: misc_feature
<222> LOCATION: (8)..(8)
<223> OTHER INFORMATION: m5c

<400> SEQUENCE: 86
aauccatngt aggtagaagu                                                20

<210> SEQ ID NO 87
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(14)
<223> OTHER INFORMATION: m6c

<400> SEQUENCE: 87
gcuaannnaa atnnaucgua                                                20

<210> SEQ ID NO 88
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(6)
<223> OTHER INFORMATION: m5c

<400> SEQUENCE: 88
aucgangaag taaatcuucu                                                20

<210> SEQ ID NO 89
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(13)
<223> OTHER INFORMATION: m5c

<400> SEQUENCE: 89
cuaacnnaaa tnnatcguag                                                20

<210> SEQ ID NO 90
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(11)
<223> OTHER INFORMATION: m5c

<400> SEQUENCE: 90
gcuggtngta natatggaac                                                20

<210> SEQ ID NO 91
<211> LENGTH: 20
<212> TYPE: DNA
<213> ORGANISM: Artificial Sequence
<220> FEATURE:
```

```
<223> OTHER INFORMATION: synthesized MSH2 gapmer sequence
<220> FEATURE:
<221> NAME/KEY: misc_feature
<222> LOCATION: (6)..(9)
<223> OTHER INFORMATION: m5c

<400> SEQUENCE: 91
aggugntnna tttgacacgu                                                    20

<210> SEQ ID NO 92
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(5)
<223> OTHER INFORMATION: m5c

<400> SEQUENCE: 92
accnnagttt gtcga                                                         15

<210> SEQ ID NO 93
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(11)
<223> OTHER INFORMATION: m5c

<400> SEQUENCE: 93
ugggaatnga ngaaguaaau                                                    20

<210> SEQ ID NO 94
<211> LENGTH: 15
<212> TYPE: DNA
<213> ORGANISM: Artificial Sequence
<220> FEATURE:
<223> OTHER INFORMATION: synthesized MSH2 gapmer sequence

<400> SEQUENCE: 94
tgaagaaaat gcgcg                                                         15

<210> SEQ ID NO 95
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (13)..(14)
<223> OTHER INFORMATION: m5c

<400> SEQUENCE: 95
accggttgag gtnntgauaa                                                    20

<210> SEQ ID NO 96
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
```

```
<222> LOCATION: (5)..(9)
<223> OTHER INFORMATION: m5c

<400> SEQUENCE: 96
tcaanaanng gttgag                                               16

<210> SEQ ID NO 97
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (5)..(11)
<223> OTHER INFORMATION: m5c

<400> SEQUENCE: 97
aatgngngan nccac                                                15

<210> SEQ ID NO 98
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (11)..(14)
<223> OTHER INFORMATION: m5c

<400> SEQUENCE: 98
aacuugatta nngnagacag                                           20

<210> SEQ ID NO 99
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (13)..(13)
<223> OTHER INFORMATION: m5c

<400> SEQUENCE: 99
ttgaagaaaa tgngcga                                              17

<210> SEQ ID NO 100
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(9)
<223> OTHER INFORMATION: m5c

<400> SEQUENCE: 100
cccntantng ggcta                                                15

<210> SEQ ID NO 101
<211> LENGTH: 17
<212> TYPE: DNA
```

```
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(10)
<223> OTHER INFORMATION: m5c

<400> SEQUENCE: 101
gccnntantn gggctaa                                                  17

<210> SEQ ID NO 102
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(15)
<223> OTHER INFORMATION: m5c

<400> SEQUENCE: 102
agcccntant ngggnuaaga                                               20

<210> SEQ ID NO 103
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(8)
<223> OTHER INFORMATION: n is a, c, g, t or u

<400> SEQUENCE: 103
ggcaagtngg ttaagaucug                                               20

<210> SEQ ID NO 104
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (11)..(14)
<223> OTHER INFORMATION: m5c

<400> SEQUENCE: 104
ugcautggtt ntanauagcc                                               20

<210> SEQ ID NO 105
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (11)..(12)
<223> OTHER INFORMATION: m5c

<400> SEQUENCE: 105
ccaauttggg nnatgaguac                                               20

<210> SEQ ID NO 106
<211> LENGTH: 20
```

```
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(7)
<223> OTHER INFORMATION: m5c

<400> SEQUENCE: 106
aaucgangaa gtaaaucuuc                                           20

<210> SEQ ID NO 107
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(14)
<223> OTHER INFORMATION: m5c

<400> SEQUENCE: 107
gcccctantn gggntaagau                                           20

<210> SEQ ID NO 108
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (11)..(12)
<223> OTHER INFORMATION: m5c

<400> SEQUENCE: 108
cggttgaggt nntgat                                               16

<210> SEQ ID NO 109
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(12)
<223> OTHER INFORMATION: m5c

<400> SEQUENCE: 109
aaatgngnga nccca                                                15

<210> SEQ ID NO 110
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(9)
<223> OTHER INFORMATION: m5c

<400> SEQUENCE: 110
ggaaungang aagtaaaucu                                           20

<210> SEQ ID NO 111
```

```
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(6)
<223> OTHER INFORMATION: m5c

<400> SEQUENCE: 111
cacnnnagtt tgtcga                                                16

<210> SEQ ID NO 112
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (6)..(10)
<223> OTHER INFORMATION: m5c

<400> SEQUENCE: 112
cuacungggn taagaugcag                                            20

<210> SEQ ID NO 113
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (12)..(12)
<223> OTHER INFORMATION: m5c

<400> SEQUENCE: 113
tgaagaaaat gngcga                                                16

<210> SEQ ID NO 114
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(14)
<223> OTHER INFORMATION: m5c

<400> SEQUENCE: 114
aaaatgngng annccac                                               17

<210> SEQ ID NO 115
<211> LENGTH: 15
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(8)
<223> OTHER INFORMATION: m5c

<400> SEQUENCE: 115
ggctggtngt acata                                                 15
```

```
<210> SEQ ID NO 116
<211> LENGTH: 17
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(13)
<223> OTHER INFORMATION: m5c

<400> SEQUENCE: 116
gaaaatgngn ganccca                                              17

<210> SEQ ID NO 117
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (7)..(12)
<223> OTHER INFORMATION: m5c

<400> SEQUENCE: 117
aaaatgngng anccca                                               16

<210> SEQ ID NO 118
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (14)..(14)
<223> OTHER INFORMATION: m5c

<400> SEQUENCE: 118
guugaagaaa atgngcgacc                                           20

<210> SEQ ID NO 119
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (10)..(13)
<223> OTHER INFORMATION: m5c

<400> SEQUENCE: 119
acuugattan ngnagacagu                                           20

<210> SEQ ID NO 120
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (8)..(16)
<223> OTHER INFORMATION: m5c

<400> SEQUENCE: 120
gaaaatgngn gannncacac                                           20
```

```
<210> SEQ ID NO 121
<211> LENGTH: 16
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (4)..(10)
<223> OTHER INFORMATION: m5c

<400> SEQUENCE: 121
gccnntantn gggcta                                                      16

<210> SEQ ID NO 122
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (9)..(15)
<223> OTHER INFORMATION: m5c

<400> SEQUENCE: 122
agaaaatgng ngannccaca                                                  20

<210> SEQ ID NO 123
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (11)..(13)
<223> OTHER INFORMATION: m5c

<400> SEQUENCE: 123
gaagaaaatg ngngacccca                                                  20

<210> SEQ ID NO 124
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (13)..(15)
<223> OTHER INFORMATION: m5c

<400> SEQUENCE: 124
uugaagaaaa tgngngaccc                                                  20

<210> SEQ ID NO 125
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (12)..(14)
<223> OTHER INFORMATION: m5c

<400> SEQUENCE: 125
ugaagaaaat gngngacccc                                                  20
```

```
<210> SEQ ID NO 126
<211> LENGTH: 20
<212> TYPE: DNA
<213> ORGANISM: Artificial Sequence
<220> FEATURE:
<223> OTHER INFORMATION: synthesized MSH2 gapmer sequence
<220> FEATURE:
<221> NAME/KEY: misc_feature
<222> LOCATION: (13)..(13)
<223> OTHER INFORMATION: m5c

<400> SEQUENCE: 126
cgggctaaga tgnaguccac                                               20

<210> SEQ ID NO 127
<211> LENGTH: 19
<212> TYPE: DNA
<213> ORGANISM: Artificial Sequence
<220> FEATURE:
<223> OTHER INFORMATION: MLH1-a siRNA

<400> SEQUENCE: 127
atacctgcca acaacttcc                                                19

<210> SEQ ID NO 128
<211> LENGTH: 19
<212> TYPE: DNA
<213> ORGANISM: Artificial Sequence
<220> FEATURE:
<223> OTHER INFORMATION: MLH1-b siRNA

<400> SEQUENCE: 128
atctgtacga accatctgg                                                19

<210> SEQ ID NO 129
<211> LENGTH: 19
<212> TYPE: DNA
<213> ORGANISM: Artificial Sequence
<220> FEATURE:
<223> OTHER INFORMATION: MLH1-d siRNA

<400> SEQUENCE: 129
tagtcgaaga atgaagata                                                19

<210> SEQ ID NO 130
<211> LENGTH: 19
<212> TYPE: DNA
<213> ORGANISM: Artificial Sequence
<220> FEATURE:
<223> OTHER INFORMATION: MSH2-a siRNA

<400> SEQUENCE: 130
tacagcacta ttcatctgc                                                19

<210> SEQ ID NO 131
<211> LENGTH: 19
<212> TYPE: DNA
<213> ORGANISM: Artificial Sequence
<220> FEATURE:
<223> OTHER INFORMATION: MSH2-b siRNA

<400> SEQUENCE: 131
gcatagttaa ggtctcttc                                                19

<210> SEQ ID NO 132
```

```
<211> LENGTH: 19
<212> TYPE: DNA
<213> ORGANISM: Artificial Sequence
<220> FEATURE:
<223> OTHER INFORMATION: MSH2-d siRNA

<400> SEQUENCE: 132
ccaaatacca atcattctc                                                    19

<210> SEQ ID NO 133
<211> LENGTH: 19
<212> TYPE: DNA
<213> ORGANISM: Artificial Sequence
<220> FEATURE:
<223> OTHER INFORMATION: MSH6-a siRNA

<400> SEQUENCE: 133
ttatttggcg gctacttcg                                                    19

<210> SEQ ID NO 134
<211> LENGTH: 19
<212> TYPE: DNA
<213> ORGANISM: Artificial Sequence
<220> FEATURE:
<223> OTHER INFORMATION: MSH6-d siRNA

<400> SEQUENCE: 134
taaccctcca tcttggccc                                                    19

<210> SEQ ID NO 135
<211> LENGTH: 19
<212> TYPE: DNA
<213> ORGANISM: Artificial Sequence
<220> FEATURE:
<223> OTHER INFORMATION: MSH6-b siRNA

<400> SEQUENCE: 135
ttattgagca tccatgtgg                                                    19

<210> SEQ ID NO 136
<211> LENGTH: 19
<212> TYPE: DNA
<213> ORGANISM: Artificial Sequence
<220> FEATURE:
<223> OTHER INFORMATION: PMS2-c siRNA

<400> SEQUENCE: 136
taagttacct tcaacatcc                                                    19

<210> SEQ ID NO 137
<211> LENGTH: 19
<212> TYPE: DNA
<213> ORGANISM: Artificial Sequence
<220> FEATURE:
<223> OTHER INFORMATION: PMS2-b siRNA

<400> SEQUENCE: 137
tagctaaaga actcataga                                                    19

<210> SEQ ID NO 138
<211> LENGTH: 19
<212> TYPE: DNA
<213> ORGANISM: Artificial Sequence
<220> FEATURE:
<223> OTHER INFORMATION: PMS2-d siRNA

<400> SEQUENCE: 138
```

```
tactccttct taatattcc                                              19
```

<210> SEQ ID NO 139
<211> LENGTH: 19
<212> TYPE: DNA
<213> ORGANISM: Artificial Sequence
<220> FEATURE:
<223> OTHER INFORMATION: PMS2-a siRNA

<400> SEQUENCE: 139

```
tatcagaaca gcttcatta                                              19
```

<210> SEQ ID NO 140
<211> LENGTH: 19
<212> TYPE: DNA
<213> ORGANISM: Artificial Sequence
<220> FEATURE:
<223> OTHER INFORMATION: POLE-a siRNA

<400> SEQUENCE: 140

```
tatttcgcct gttcctcgc                                              19
```

<210> SEQ ID NO 141
<211> LENGTH: 19
<212> TYPE: DNA
<213> ORGANISM: Artificial Sequence
<220> FEATURE:
<223> OTHER INFORMATION: POLE-b siRNA

<400> SEQUENCE: 141

```
atacgaagca ccctcctcc                                              19
```

<210> SEQ ID NO 142
<211> LENGTH: 19
<212> TYPE: DNA
<213> ORGANISM: Artificial Sequence
<220> FEATURE:
<223> OTHER INFORMATION: POLE-d siRNA

<400> SEQUENCE: 142

```
taatcttcca gcttccgag                                              19
```

<210> SEQ ID NO 143
<211> LENGTH: 19
<212> TYPE: DNA
<213> ORGANISM: Artificial Sequence
<220> FEATURE:
<223> OTHER INFORMATION: POLD1-b siRNA

<400> SEQUENCE: 143

```
acccaaacat gctctctcg                                              19
```

<210> SEQ ID NO 144
<211> LENGTH: 19
<212> TYPE: DNA
<213> ORGANISM: Artificial Sequence
<220> FEATURE:
<223> OTHER INFORMATION: POLD1-a siRNA

<400> SEQUENCE: 144

```
taatggtcaa tctccaact                                              19
```

METHODS OF TREATING CANCER AND/OR ENHANCING SENSITIVITY TO CANCER TREATMENT BY INCREASING TUMOR MUTATION BURDEN OR TUMOR INDELS

This application is the U.S. National stage of International Application No. PCT/CA2018/051341, entitled, "METHODS OF TREATING CANCER AND/OR ENHANCING SENSITIVITY TO CANCER TREATMENT BY INCREASING TUMOR MUTATION BURDEN OR TUMOR INDELS" by Mark David Vincent, filed 23 Oct. 2018, published in English, which claims the benefit of U.S. Provisional Application No. 62/646,543, by Mark David Vincent, filed 22 Mar. 2018; which claims the benefit of U.S. Provisional Application No. 62/646,147, by Mark David Vincent, filed 21 Mar. 2018; which claims the benefit of U.S. Provisional Application No. 62/580,570, by Mark David Vincent, filed 2 Nov. 2017; and which claims the benefit of U.S. Provisional Application No. 62/575,708, by Mark David Vincent, filed 23 Oct. 2017. The entire teachings of the above applications are incorporated herein by reference.

FIELD OF THE INVENTION

The present invention relates to the field of cancer therapy and, in particular, to methods of treating cancer and/or enhancing sensitivity to cancer treatment by increasing tumor mutation burden or tumor indels.

REFERENCE TO A SEQUENCE LISTING

This application includes a Sequence Listing submitted electronically as a text file named 857-130PCTsequencelisting_ST25revisedv5 created on Jul. 25, 2024, with a size of 3400 bytes and comprising 144 sequences. The sequence listing is hereby incorporated by reference.

BACKGROUND OF THE INVENTION

Immune checkpoint inhibition is the therapeutic standard-of-care in a range of human cancers, including, many that are advanced and incurable. The FDA has approved immune checkpoint blockade treatment for a variety of cancers including melanoma, small cell and non-small cell lung cancer, head and neck cancer, kidney cancer, Hodgkin's Disease, Merkel cell tumor, liver cancer, stomach cancer and bladder cancer (O'Connor J M et al *JAMA Oncology* August 1 ;4(8):e180798.; Jardim D L et al *Clin Ca Res* 2018 April 15; 24(8):1785-1794. doi: 10.1158/1078-0432.CCR-17-1970. Epub 2017 Dec. 6). Immune checkpoint inhibitors ('ICI') are also considered potential therapeutics for other cancers including non-Hodgkin's lymphoma (Jacobson C A and Armand P *Best Pract Res Clin Haematol.* 2018 Sep.; 31(3):299-305. doi: 10.1016/j.beha.2018.07.015. Epub 2018 Jul. 23).

It is widely recognized in clinical oncology that ICI therapy only works well in a minority of patients with significant tumor shrinkage often occurring in less than 50% of clinical trial populations. In other patients, their tumors may stabilize for a period of time, but in the remainder of the patients the tumors keep on growing. Even in those who benefit from ICI, the benefit is usually temporary with the majority of patients relapsing and dying within a few years (Wolchok, J D et al NEJM 2017; 377: 1345-1356; Vokes EE et al *Ann Oncol.* 2018 Apr. 1; 29(4):959-965). Conventional cytotoxic chemotherapy and radiotherapy may be used in conjunction with ICI to improve long term prognosis (Gandhi L et al *N Engl J Med.* 2018 May 31; 378(22):2078-2092).

Tumor mutation burden (TMB) is a measure of the mutations in a tumor cell and is defined as the number of somatic, coding, base substitution, and insertion and deletion (indel) mutations per megabase of genome examined (Chalmers et al. *Genome Medicine* (2017) 9:34). Tumor mutations are widely acknowledged to be the source of the acquired, 'non-self' antigens ('neo-antigens') that mark cancers as foreign to the host immune system (Schumacher T N and Schreiber R D *Science.* 2015 Apr. 3; 348(6230):69-74). Evidence suggests that the indel mutations result in more neo-antigens compared to mutations resulting in single nucleotide variations. Although a subset of tumor mutations is causally implicated in the pathogenesis of the cancer, many mutations are simply reflective of the genomic instability of cancers in general and do not promote the growth of the cancer (McFarland C D et al *Proc Natl Acad Sci USA.* 2014 Oct. 21; 111(42):15138-43). These 'passenger' mutations can contribute to the antigenicity of the cancer and thus can impact prognosis.

Whether or not the cancer is sufficiently antigenic to be controlled by the immune system depends in part on the number of mutations in the cancer. Different types of cancer vary substantially in their TMB. Cancers which can best be treated by ICI are melanoma and non-small cell lung cancer (squamous and non-squamous) which on average together are the top three most mutated cancers, and therefore likely to harbor the highest proportion of neo-antigens (Schumacher T N and Schreiber R D, ibid).

Even within cancer types there is significant variation in TMB. This can be quantified in terms of the whole exomic (protein-coding gene) mutations per tumor or more commonly as 'mutations per megabase' (Mb) by whole exome sequencing ('WES') or estimated by sequencing a smaller panel of protein-coding genes. Neo-antigens are unlikely to occur when the TMB is <1/Mb, occur 'occasionally' if the TMB is <10/Mb, occur 'regularly' if the TMB is between 10 and 20/Mb and occur 'frequently' when the TMB is >20/Mb (Schumacher T N and Schreiber R D, ibid).

High TMB has been correlated with an increased effectiveness of ICI therapy. For example, the CM 227 trial studied the combination of the ICI ipilumumab and nivolumab in advanced non-small cell lung cancer and found the major benefit for this combination to be in patients with a TMB>10 (Hellman MD et al NEJM 2018; 10378: 20193-2014), corroborating a previous exploratory trial, CM 568. (Ramalingam S S et al. *Presented at the American Association for Cancer Research* 2018 Annual Meeting, Chicago, Apr. 16, 2018). Rizvi et al (Rizvi N et al *Science* 2015; 348: 124-128) found that in two independent cohorts of advanced non-small cell lung cancer patients treated with the ICI pembrolizumab, clinical benefit was strongly associated with non-synonymous TMB.

A similar situation is developing in small cell lung cancer, treated by ICI (Boumber JTD, 2018 doi: 10.21037/jtd.2018.07.120). A study of nivolumab with and without ipilumumab showed that small cell lung cancer patients with the highest TMB (expressed here as >248 mutations per whole exome) experienced most benefit from the ICI (Hellmann M D et al *Cancer Cell* 2018; 33:853-61).

Association between TMB and benefit from ICI have also been seen in cancers other than lung cancer, such as melanoma, colon, breast, Merkel cell, bladder, cervix, ovary, head and neck and liver (Johnson D M et al *Cancer Immunol Res.* 2016 Nov.; 4(11):959-967; Goodman A et al *Mol Cancer Ther* 2017; 16(11); 2598-608).

Genomic stability is maintained by the fidelity of DNA replication and by mismatch repair. Defects in either DNA polymerases that result in decreased DNA replication fidelity or defects in the DNA mismatch repair (MMR) system increase genomic instability.

The proofreading functions of DNA polymerases are critical to ensure high fidelity synthesis of DNA during replication and DNA repair. Polymerase δ and Polymerase E are high fidelity DNA polymerases responsible for the bulk of DNA synthesis during replication. Missense mutations in the exonuclease domains of these enzymes results in a hypermutator phenotype. Both germline and somatic defects in exonuclease domains of these polymerases have been found in a variety of cancers.

There are a number of proteins in the MMR system and include MLH1, MLH3, MSH2, MSH3, MSH6, PMS1 and PMS2. The functions of the MMR system include correction of errors that may arise during DNA replication and recombination and repair of DNA damage. Failure to correct errors or repair damage in oncogenes and tumor suppressor genes may result in cells undergoing malignant transformation and the development of cancer. Hereditary defects in this system are found in hereditary nonpolyposis colon cancer (HNPCC). In addition, defects of the MMR system may be involved in pathogenesis of non-hereditary sporadic cancer.

MMR deficiencies lead to DNA damage tolerance, which contributes to increased mutagenicity, tumor heterogeneity and chemoresistance. Drugs that target the MMR system are being developed which either restore functionality of the MMR system or inhibit function. Inhibition of MMR function may cause the cell lethality by preventing the damage from being repaired. In addition, MMR deficiencies can lead to the development of neo-antigens and therefore MMR deficient cancers may have higher antigenicity which may make such cancers candidates for immunotherapy.

Patients with certain congenital or acquired defects in DNA repair apparatus develop cancers with extraordinarily high rates of tumor mutations; furthermore, these tumors are much more likely to respond to ICI therapy. The most widely recognized examples of this phenomenon involve colorectal cancer patients with defects in the DNA mismatch repair (MMR) system. About 15% of incident colorectal cancers occur as a result of mutations in one of the four main genes responsible for MMR, namely MLH1, PMS2, MSH2 and MSH6. In one third of these, the defect is inherited ('Lynch Syndrome') but in two thirds it is acquired, occurring typically in elderly females. Being highly mutated these cancers are believed to be correspondingly highly immunogenic, and therefore spontaneously controlled by the unaided immune system most of the time. Consequently, they rarely become metastatic; only 4% of advanced colorectal cancers are MMR defective. Nonetheless, in these patients, the response rate to ICI is very high which is not at all the case with the vast majority of colorectal cancers arising in the more usual way, and which contain much smaller numbers of mutations. Defective MMR also occurs in some other types of cancer (eg biliary tract cancer, stomach cancer) and these tumors are also much more likely to respond to ICI (Le DT et al *N Engl J Med*. 2015 Jun. 25; 372(26):2509-20). Sequencing revealed a mean TMB of 1782 mutations per tumor in the MMR deficient patients, vs only 73 per tumor in the MMR proficient patients. Furthermore, prolonged progression-free survival is associated with high somatic mutation loads.

MMR defects result in a high incidence of insertion and deletion mutations in repeat DNA sequences ('microsatellites') and if these are contained in exons, this leads to frameshift mutations which are felt to be particularly immunogenic (Mlecnik L et al. Immunity 44, 698-711; Baretti M and Le DT, *Pharmacology and Therapeutics* 2018; 189: 45-62). MMR deficient cancers also exhibit high rates on base substitutions (approximately 1300 in MMR deficient colorectal cancers vs 190 in MMR proficient colorectal cancers)(Baretti M and Le D T, ibid). In the important paper by Chalmers and colleagues (Chalmers Z R et al ibid), 97% of their MSI-H patients had TMB 0 mutations/Mb; MSI-H (microsatellite instability high) is a sign of MMR deficiency. Chalmers et al also confirmed that DNA polymerase E (POLE') mutation may be associated with hypermutation, occurring often in patients with endometrial cancer. Furthermore, some patients with melanoma had inactivating mutations in the PMS2 gene (a MMR gene) and exhibited>fivefold increases in TMB. The average for all the tumors analyzed by Chalmers et al was 3.6/Mb.

Occasionally, patients may inherit a defective MMR gene from both parents, resulting in a syndrome known as bi-allelic MMR deficiency ('bMMRD'). These children are prone to cancer at very young ages, but if detected and diagnosed correctly, may respond to ICI as the TMB of their cancers is extremely high; the so-called 'ultra-hypermutated' TMB. Also responsible for this are POLE mutations (Santin ad et al *Clin Cancer Res*. 2016 Dec. 1; 22(23):5682-5687). In these cases, especially when POLE and MMR deficiency co-occur as they might (since the one can lead to the other in either direction) the TMB might reach >20,000 per exome (Bouffet et al *J Clin Oncol* 2016; 34: 2206-2211). These authors describe two cases (siblings) of bMMRD associated with POLE mutations, both children having recurrent glioblastoma, in which the very high TMB enabled responses to the ICI nivolumab.

Kandoth et al sequenced endometrial cancers and classified them into four groups, including an ultrahypermutated group (mean TMB of 232/Mb), associated with POLE mutations (especially in the POLE subnit 1); and an hypermutated group (18/Mb), associated with MLH1 promoter hypermethyation (which silences the gene) (Kandoth et al, *Nature* 2013; 497:67-73). It is known that de-activating mutation in either POLE or POLD1 can result in hypermutation (Lange S S et al *Nat Rev Cancer* 2011; 11:96-110; Briggs S et al *J Pathol*. 2013; 230:148-53; see also *Henninger and Pursell IUBMB Life*. 2014 May; 66(5):339-51. doi: 10.1002/iub.1276. Epub 2014 May 24.DNA polymerase ε and its roles in genome stability) due to the loss in proofreading capacity, which normally removes mis-incorporated bases (a functionality then doublechecked by the MMR proteins). POLE (and POLD1) loss-of-function mutations are well-described to be causally implicated in the pathogenesis of some colorectal cancers and endometrial cancers, even without the additional contribution of MMR defects; in these cases the TMB is also high (Church D N et al *Human Molecular Genetics* 2013; 22: 2820-2828). The mutations in POLE and POLD1 affect in particular the proofreading function of these polymerases, and involve the exonuclease functionality underlying the proofreading capability. Furthermore, these mutations may be pathogenic in the heterozygous state, not necessarily requiring a complete loss of function. Cancers from The Cancer Genome Atlas with these polymerase mutations demonstrated striking increments in hypermutation, averaging 6811 exonic base substitutions per tumor compared to 174 in cancers lacking these POLE or POLD1 mutations (Church DN et al ibid 2013), despite lacking evidence of associated MMR mutational defects. Nonetheless, co-occurrence of a POL mutation and an MMR mutation is well described (Jansen A M L et al EJHG 2016; 24:1089-1092; Bouffet et al 2016 ibid) and is often associated with hypermutation (10-100/Mb) or even ultrahypermution (>100 variants/Mb).

Since the propensity to develop immunologically relevant neoantigens is a function of the TMB, it follows that the known responsiveness of these hypermutant and ultrahypermutant cancers is very likely to be related to an exceptionally high neoantigen burden.

Germano et al who showed that pre-implantation CRISP/Cas9 knockout of the MLH1 analogue in mice generated a murine tumor which could be more easily controlled by co-administered ICI (Germano G et al *Nature* 2017; 552: 116-123; published 7 Dec. 2017) than tumors with intact MLH1 function. They confirmed that MLH1 knockout resulted in 'augmented mutational load that resulted in an increased number of predicted neoantigens which evolved dynamically over time.'

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide methods of treating cancer and/or of enhancing sensitivity to cancer treatment by increasing tumor mutation burden or tumor indels.

In accordance with one aspect of the present invention, there is provided a method of increasing tumor mutation burden of a cancer in a subject comprising administering to the subject an effective amount of a therapeutic that inhibits at least one DNA mismatch repair enzyme and/or polymerase proofreading. In accordance with one embodiment, the DNA mismatch repair enzyme is MSH2, MLH1, MSH6 or PMS2 and the polymerase is polδ or polε. In some embodiments, the therapeutic is a DNA mismatch repair enzyme antibody, CRISPR, peptide, aptamer or antisense therapeutic.

In accordance with another aspect of the present invention, there is provided a method of treating cancer in a subject comprising administering to the subject an effective amount of a therapeutic that inhibits at least one DNA mismatch repair enzyme and/or polymerase proofreading. In some embodiments, the method further comprises administering an immunotherapeutic.

In accordance with another aspect of the present invention, there is provided an antisense therapeutic comprising a sequence complementary to an mRNA encoding a DNA mismatch repair enzyme or a portion of the mRNA.

In accordance with another aspect of the present invention, there is provided an antisense therapeutic that targets polδ or polε.

In accordance with one aspect of the present invention, there is provided a method of treating cancer in a subject comprising administering to the subject an effective amount of therapeutic directed against a DNA mismatch repair enzyme. In accordance with one embodiment, the therapeutic targets MSH2, MLH1 or both MSH2 and MLH1.

In some embodiments, the therapeutic targets MSH6 and/or PMS2.

In accordance with one embodiment of the invention, the therapeutic is a DNA mismatch repair enzyme antibody, CRISPR, peptide, aptamer or antisense therapeutic.

In accordance with one aspect of the present invention, there is provided a method of treating cancer in a subject comprising administering to the subject an effective amount of an antisense therapeutic comprising a sequence complementary to an mRNA encoding a DNA mismatch repair enzyme or a portion of the mRNA. In accordance with one embodiment, the antisense therapeutic targets MSH2, MLH1 or both MSH2 and MLH1. In some embodiments, the antisense therapeutic targets MSH6 and/or PMS2

In accordance with another aspect of the present invention, there is provided an antisense therapeutic comprising a sequence complementary to an mRNA encoding a DNA mismatch repair enzyme or a portion of the mRNA. In accordance with one embodiment, the antisense therapeutic targets MSH2 or MLH1. In some embodiments, the antisense therapeutic targets MSH6 and/or PMS2. In some embodiments the antisense therapeutic include siRNA, shRNA or antisense oligonucleotides.

In accordance with another aspect of the present invention, there is provided a method of treating cancer in a subject comprising administering to the subject an effective amount of a DNA mismatch repair enzyme antisense therapeutic in combination with an immunotherapeutic. In accordance with some embodiments, the immunotherapeutic is an immune checkpoint inhibitor. In accordance with some embodiments, the immunotherapeutic is an agent or combination of agents that enhance the immune system to recognize and kill tumor cells.

In accordance with some embodiments the immune checkpoint inhibitor comprises anti-PD-1, anti-PDL1, anti-CTLA4, and other agents.

In accordance with another aspect of the invention, there is provided a method to increase a visibility of a cancer to the immune system in a subject comprising administering to the subject an effective amount of an antisense therapeutic comprising a sequence complementary to an mRNA encoding a DNA mismatch repair enzyme or a portion of the mRNA.

In accordance with one embodiment, the cancer to be treated is colorectal cancer and in particular, colorectal cancer that is not mismatch repair defective.

In accordance with one embodiment, the cancer to be treated is glioblastoma, lung cancer or melanoma.

In accordance with another aspect of the invention, there is provided a method of treating cancer in a subject comprising administering to the subject an effective amount a CRISPR therapeutic that targets DNA mismatch repair enzyme.

In accordance with another aspect of the invention, there is provided a method of inhibiting cancer cell proliferation comprising administering to the cell an effective amount of a therapeutic that inhibits at least one DNA mismatch repair enzyme and/or polymerase proofreading.

In accordance with another aspect of the invention, there is provided a method of increasing indel mutations of a cancer in a subject comprising administering to the subject an effective amount of a therapeutic that inhibits at least one DNA mismatch repair enzyme and/or polymerase proofreading.

BRIEF DESCRIPTION OF THE FIGURES

These and other features of the invention will become more apparent in the following detailed description in which reference is made to the appended Figures.

FIG. 4 details impact of siRNA on relative DNA content of A549b and U87 cells.

FIG. 5b details dose response analysis of gapmers of FIG. 5a.

FIGS. 6a to 6d details impact of siRNA on TMB in U87, A549b, SK-MEL-5 and HT-29 cells. In particular, shown in FIG. 6A are U87 glioblastoma cell line alterations (brain cancer) caused by MMR and POLE downregulation by siRNA; shown in FIG. 6B are A549 lung cancer cell line alterations caused by MMR and POLE downregulation by siRNA; shown in FIG. 6C are SK-MEL-5 melanoma cell line alterations caused by MMR and POLE downregulation by siRNA and shown in FIG. 6D are HT-29 colon cancer cell line alterations caused by MMR and polymerase proofreading activity.

FIG. 7 details impact of various gapmers targeting MSH2 on relative mRNA levels in HELA cells.

DETAILED DESCRIPTION OF THE INVENTION

Figure 1:
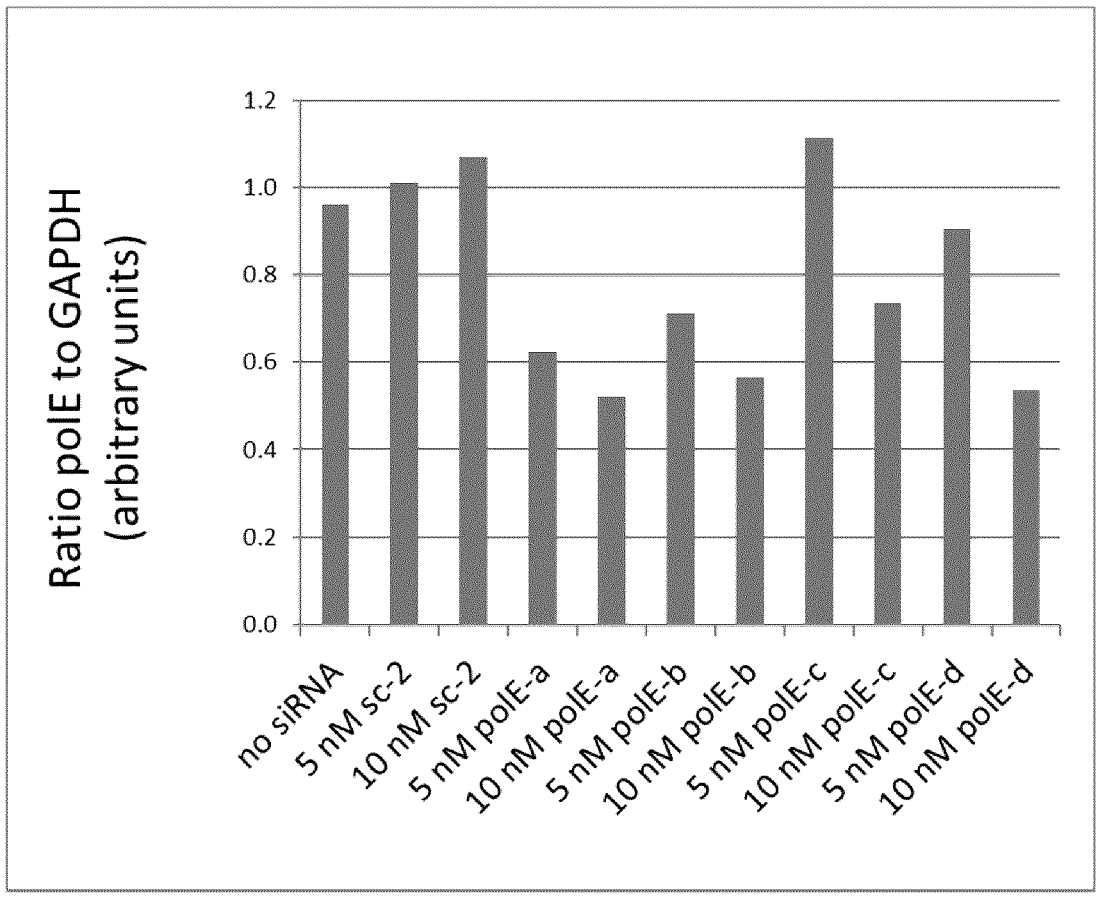
FIG. 1 details impact of siRNAs on POLE1 levels as determined by qPCR.
Figure 2:
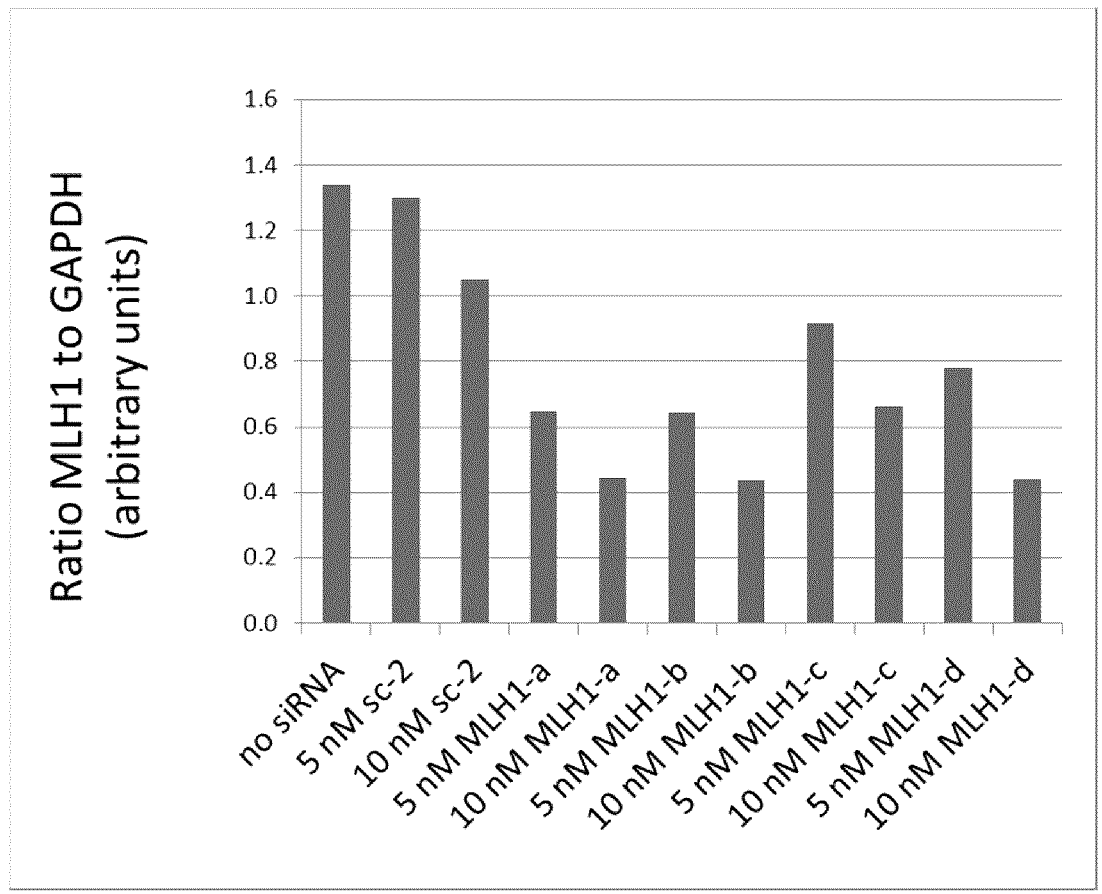
FIG. 2 details impact of siRNAs on MLH1 levels as determined by qPCR.

The immune system can recognize highly mutated cancer cells that include neo-antigens as foreign. A number of cancer therapies act by enhancing the immune response, for example by enhancing the capacity of the human immune system to recognize and kill human tumor cells. As of 2017, the FDA had approved the use of immune checkpoint inhibitors to treat six different types of cancers. Examples of approved therapeutics include anti-CTLA-4 therapeutics such as Ipilimumab, anti-PD-1 inhibitors including Nivolumab, Pembrolizumab, and Spartalizumab and PD-L1 inhibitors such as Atezolizumab, Avelumab and Durvalumab.

Responsiveness to these treatments may be improved by increasing the visibility of cancer cells to the immune system, i.e. by increasing the number of neo-antigens. One embodiment of the present invention is to increase the visibility of cancer cells to the immune system by decreasing DNA replication fidelity and/or inhibiting DNA mismatch repair thereby increasing the number of neoantigens.

One embodiment of the present invention, therefore, provides for the use of therapeutics targeted against DNA polymerase proofreading activity and/or therapeutics that target mismatch repair enzymes to increase the number of neoantigens. Optionally, these therapeutics are used in combination with immunotherapeutics that either enhance immune response or inhibit immune check points. Without being limited by any particular theory, the efficacy of such combinations may be due to the fact that inhibition of mismatch repair in cancer cells will increase the number of neoantigens. As such, cancer cells with increased neoantigens are likely to be more vulnerable to the immune system and cancer immunotherapies. Accordingly, treatment of cancer patients with therapeutics targeted against DNA polymerase proofreading activity and/or therapeutics that target mismatch repair enzyme can result in improved immune response to the cancer.

Optionally, methods of the invention comprise a step of assessing tumor mutation burden (TMB) and/or the activity of DNA mismatch repair enzymes and/or DNA polymerase proofreading activity. In some embodiments, DNA mismatch repair enzymes and/or DNA polymerase proofreading activity are targeted based on the TMB of the tumor and/or status of DNA repair and/or DNA replication fidelity.

In some embodiments, therapeutics targeted against DNA polymerase proofreading activity target the proofreading activity of polδ or polε and/or the therapeutics targeted against DNA mismatch repair enzymes target MLH1, MSH2, MSH6 or PMS2. In some embodiments, a combination of therapeutics that target DNA polymerase proofreading activity and/or DNA mismatch repair enzymes are used.

The therapeutics against DNA polymerase proofreading activity and/or the therapeutics targeted against DNA mismatch repair enzymes include antibodies, aptamers, peptides, CRISPR therapeutics and antisense therapeutics including antisense oligonucleotides, siRNA, shRNA, gapmers and RNAi.

These therapeutics can be used in the treatment of cancer as single agents (including the use of combinations of the therapeutics that increase TMB) or they may be used in combination with other cancer therapies including immunotherapeutics or chemotherapeutics.

In accordance with one embodiment of the invention, therapeutics against DNA polymerase proofreading activity and/or the therapeutics targeted against DNA mismatch repair enzymes are antisense therapeutics used to induce a decrease in expression in the targeted protein thereby increasing the number of neoantigens in the cancer cell. Accordingly, the methods provided by the present invention are applicable to a wide variety of cancers. In accordance with one embodiment of the invention, the antisense therapeutic is used to induce a decrease in expression in the targeted mismatch repair enzyme thereby increasing the number of neoantigens in the cancer cell allowing the patient to obtain greater benefit from immunotherapeutics including immune checkpoint inhibitors.

As an example, the antisense therapeutics may potentiate the effects of drugs such as the immune check point inhibitors such as ipilimumab (Yervoy), which targets the immune checkpoint CTLA-4, and nivolumab (Opdivo), which targets the immune checkpoint PD-1.

In some embodiments, the therapeutic is CRISPR based and results in loss or reduction of polo and/or polε proofreading. In some embodiments, the CRISPR based therapeutic introduces missense mutations into polE. Missense mutations that impact polε proofreading are known in the art and include Phe367Ser, Leu424Val, Val411Leu and Arg286His.

In some embodiments, the CRISPR based therapeutic introduces missense mutations into polδ. Missense mutations that impact polδ proofreading are known in the art and include POLD1 Ser478Asn.

The present invention also provides for methods of treating cancer using a therapeutic directed against polε subunit 1. The therapeutics include antibodies, aptamers, peptides and antisense therapeutics.

In some embodiments, the CRISPR based therapeutic introduces missense mutations into polE subunit 1. Missense mutations introduced in subunit 1 include P286R and V411L or others that occur in ultrahypermutated tumors.

In some embodiment, the methods of the invention are used in combination with antisense therapeutics that target a nucleic acid encoding a double strand DNA repair protein. In one embodiment, the method is used in conjunction with inhibition of BRCA2.

In other embodiments, the method may function by increasing genomic instability to a level that exhibits incapability with cellular viability and/or growth.

Definitions

Unless defined otherwise, all technical and scientific terms used herein have the same meaning as commonly understood by one of ordinary skill in the art to which this invention belongs.

The term "antisense therapeutic," as used herein, refers to a therapeutic comprising a sequence that is complementary to the mRNA transcribed from a target gene. In the context of the present invention, the target gene is a gene encoding polε subunit 1, subunit 3 and/or subunit 4 or a mismatch repair protein such as, for example, MLH1, MSH2, MSH6 and PMS2. The antisense therapeutics can include siRNA, shRNA, antisense oligonucleotides, RNAi, CRISPR systems or silencing RNA. CRISPR based therapeutic may be used to introduce missense mutations in polδ and/or polε proofreading domains. The therapeutics may include appropriate delivery systems or carriers as is known in the art. In some embodiments, the therapeutic is formulated for regional perfusion into body cavities and/or compartments, including intraperitoneal perfusion, intrapleural perfusion, hepatic perfusion and installation into the central nervous system.

The term "anti-proliferative" or "anti-proliferative activity", as used herein, means a reduction in total cell number in treated versus control. OLIGOs that have an anti-proliferative activity include those OLIGOs that are cytotoxic, induce apoptosis, arrest or delay the cell cycle, alter cell size, or are a combination thereof.

The term "oligonucleotide," as used herein, means a polymeric form of nucleotides of at least 7 nucleotides in length comprising either ribonucleotides or deoxynucleotides or modified forms of either type of nucleotide. The term includes single and double stranded forms of DNA or RNA. In general, oligonucleotides are between about 7 and about 100 nucleotides in length.

"Relative cell density" refers to the relative density of live cells at the end of an assay.

The term "selectively hybridize" as used herein refers to the ability of a nucleic acid molecule to bind detectably and specifically to a second nucleic acid molecule. Oligonucleotides selectively hybridize to target nucleic acid strands under hybridization and wash conditions that minimize appreciable amounts of detectable binding to non-specific nucleic acid molecules. High stringency conditions can be used to achieve selective hybridization conditions as known in the art and discussed herein.

Typically, hybridization and washing conditions are performed at high stringency according to conventional hybridization procedures. Washing conditions are typically 1-3× SSC, 0.1-1% SDS, 50-70° C. with a change of wash solution after about 5-30 minutes.

The term "corresponds to" as used herein with reference to nucleic acid sequences means a polynucleotide sequence that is identical to all or a portion of a reference polynucleotide sequence.

The term "complementary to" is used herein to mean that the polynucleotide sequence is identical to all or a portion of the complement of a reference polynucleotide sequence.

The following terms are used herein to describe the sequence relationships between two or more polynucleotides: "reference sequence," "window of comparison," "sequence identity," "percent (%) sequence identity" and "substantial identity." A "reference sequence" is a defined sequence used as a basis for a sequence comparison; a reference sequence may be a subset of a larger sequence, for example, as a segment of a full-length cDNA, mRNA or gene sequence, or may comprise a complete cDNA, mRNA or gene sequence. Generally, a reference polynucleotide sequence is at least 20 nucleotides in length, and often at least 50 nucleotides in length.

A "window of comparison", as used herein, refers to a conceptual segment of the reference sequence of at least 15 contiguous nucleotide positions over which a candidate sequence may be compared to the reference sequence and wherein the portion of the candidate sequence in the window of comparison may comprise additions or deletions (i.e. gaps) of 20 percent or less as compared to the reference sequence (which does not comprise additions or deletions) for optimal alignment of the two sequences. The present invention contemplates various lengths for the window of comparison, up to and including the full length of either the reference or candidate sequence. In one embodiment, the window of comparison is the full length of the candidate sequence. Optimal alignment of sequences for aligning a comparison window may be conducted using the local homology algorithm of Smith and Waterman (*Adv. Appl. Math.* (1981) 2:482), the homology alignment algorithm of Needleman and Wunsch (*J. Mol. Biol.* (1970) 48:443), the search for similarity method of Pearson and Lipman (*Proc. Natl. Acad. Sci.* (*U.S.A.*) (1988) 85:2444), using computerised implementations of these algorithms (such as GAP, BESTFIT, FASTA, and TFASTA in the Wisconsin Genetics Software Package Release 7.0, Genetics Computer Group, 573 Science Dr., Madison, WI), using publicly available computer software such as ALIGN or Megalign (DNASTAR), or by inspection. The best alignment (i.e. resulting in the highest percentage of identity over the comparison window) is then selected.

The term "sequence identity" means that two polynucleotide sequences are identical (i.e. on a nucleotide-by-nucleotide basis) over the window of comparison.

The term "percent (%) sequence identity," as used herein with respect to a reference sequence is defined as the percentage of nucleotide residues in a candidate sequence that are identical with the residues in the reference polynucleotide sequence over the window of comparison after optimal alignment of the sequences and introducing gaps, if necessary, to achieve the maximum percent sequence identity, without considering any conservative substitutions as part of the sequence identity.

The term "substantial identity" as used herein denotes a characteristic of a polynucleotide sequence, wherein the polynucleotide comprises a sequence that has at least 50% sequence identity as compared to a reference sequence over the window of comparison. In various embodiments of the invention, polynucleotide sequences having at least 60% sequence identity, at least 70% sequence identity, at least 80% sequence identity, at least 90% sequence identity and at least 95% sequence identity as compared to a reference sequence over the window of comparison are considered to have substantial identity with the reference sequence.

The terms "therapy" and "treatment," as used interchangeably herein, refer to an intervention performed with the intention of improving a recipient's status. The improvement can be subjective or objective and is related to the amelioration of the symptoms associated with, preventing the development of, or altering the pathology of a disease, disorder or condition being treated. Thus, the terms therapy and treatment are used in the broadest sense, and include the prevention (prophylaxis), moderation, reduction, and curing of a disease, disorder or condition at various stages. Prevention of deterioration of a recipient's status is also encompassed by the term. Those in need of therapy/treatment include those already having the disease, disorder or condition as well as those prone to, or at risk of developing, the disease, disorder or condition and those in whom the disease, disorder or condition is to be prevented.

The term "ameliorate" or "amelioration" includes the arrest, prevention, decrease, or improvement in one or more the symptoms, signs, and features of the disease being treated, both temporary and long-term.

The term "subject" or "patient" as used herein refers to a mammal in need of treatment.

Administration of the compounds of the invention "in combination with" one or more further therapeutic agents, is intended to include simultaneous (concurrent) administration and consecutive administration. Consecutive administration is intended to encompass administration of the therapeutic agent(s) and the compound(s) of the invention to the subject in various orders and via various routes.

As used herein, the term "about" refers to an approximately +/−10% variation from a given value. It is to be understood that such a variation is always included in any given value provided herein, whether or not it is specifically referred to.

Target Proteins

The tumor mutation burden, in whole or in part, may be increased by decreasing the replication fidelity of DNA polymerases and/or by inhibiting DNA mismatch repair.

DNA Polymerase Targets:

The activities of DNA polymerases are essentially for DNA synthesis during replication and during DNA repair. DNA polymerases involved in DNA synthesis during replication include Polα, Polδ and Polε, with Polδ and Polε being responsible for DNA synthesis after primer extension and thus responsible for the bulk of DNA synthesis. Both Polδ and Polε have exonuclease domains that increase replication fidelity. Mutations in the exonuclease domains result in a dramatic increase in base substitutions.

Polδ consists of four subunits: POLD1, POLD2, POLD3, and POLD4. Accordingly, in some embodiments, the therapeutic targets one of the subunits. In alternative embodiments, the therapeutic has multiple components and targets one or more of the subunits.

Polε consists of four subunits: POLE1, POLE2, POLE3, and POLE4. Accordingly, in some embodiments, the therapeutic targets one of the subunits. In alternative embodiments, the therapeutic has multiple components and targets one or more of the subunits.

DNA Repair Targets

Cells comprise distinct pathways for mediating the repair of different types of DNA damage. Such pathways include base excision repair, homologous recombination-dependent DNA double strand break (HR-DD) repair, non-homologous end-joining (NHEJ), nucleotide excision repair, and mismatch repair. HR-DD repair and NHEJ pathways are responsible for the repair of double strand DNA breaks (DSBs). Antisense therapeutics according to the present invention target nucleic acids that encode proteins in the mismatch repair pathway.

In one embodiment, antisense therapeutics for use in accordance with the present invention are designed to target a nucleic acid encoding a DNA repair protein, wherein the DNA repair protein is involved in mismatch repair. Non-limiting examples of key proteins that are involved in this pathway include, for example, MLH1, MSH2, MSH6 and PMS2. In one embodiment, antisense therapeutics for use in accordance with the present invention are designed to target a nucleic acid encoding MLH1, MSH2, MSH6 and PMS2.

Antisense Therapeutics

Selection and Characteristics

Antisense therapeutic for use in accordance with the present invention are designed to target a nucleic acid encoding POLD1, POLD2, POLD3, POLD4, POLE1, POLE2, POLE3, POLE4 or a nucleic acid encoding a mismatch repair protein including MLH1, MSH2, MSH6 and PMS2.

The sequences of the genes and the protein sequences are known in the art. For example, the sequence of the POLD1 mRNA is available under GenBank™ Accession No. NM_001256849; NM_001308632; NM_002691; NM_001256849.1; NM_001308632.1 and others. The sequence of the POLD2 mRNA is available under GenBank™ Accession No. NM_001127218; NM_001256879; NM_006230; NM_008894; and others. The sequence of the POLD3 mRNA is available under GenBank™ Accession No. NM_006591; NM_133692 and others. The sequence of the POLD4 mRNA is available under GenBank™ Accession No. NM_001256870; NM_021173; NM_027196 and others.

The sequence of the POLE1 mRNA is available under GenBank™ Accession No. NM_006231; NM_006231.3; NM_011132; and others. The sequence of the POLE2 mRNA is available under GenBank™ Accession No. NM_001197330; NM_001197331; NM_002692; NM_001348384; NM_001348385; NM_011133; and others. The sequence of the POLE5 mRNA is available under GenBank™ Accession No. NM_001278255; NM_017443; NM_021498 and others. The sequence of the POLE4 mRNA is available under GenBank™ Accession No. NM_019896; NM_025882 and others.

The sequences of the genes of various mismatch repair enzymes are known in the art. For example, the sequence of the MLH1 mRNA is available under GenBank™ Accession No. NM_000249; NM_000249.3; NM_001167617; NM_001167618 NM_001167619; NM_001258271; and others. Likewise, the sequences of the MSH2 mRNA (GenBank™ Accession No. NM_000251; M_000251.2), MSH6 mRNA (GenBank™ Accession No. NM_000179.2; NM_001281492.1; NM_001281493.1; NM_001281494.1; U54777.2; AY082894.1), PMS2 mRNA (GenBank™ Accession No. NM_000535.6; NM_001322013.1 and others) are also publicly available.

In targeting the antisense therapeutic to the selected gene, a determination is made of a site or sites within this gene or it's mRNA for the antisense interaction to occur such that the desired effect, for example, modulation of expression of the protein encoded by the gene and/or inhibition of cancer cell growth or proliferation, will result. Once the target site or sites have been identified, oligonucleotides are chosen that are sufficiently complementary (i.e. hybridize with sufficient strength and specificity) to the target to give the desired result.

Antisense therapeutic can be targeted to the 5' untranslated region (5'-UTR), the translation initiation or start codon region, the coding sequence (or open reading frame (ORF)), the translation termination or stop codon region, or the 3' untranslated region (3'-UTR) of a gene. One embodiment of the present invention provides for antisense oligonucleotides targeted to the coding region or the 3'-UTR of the target mRNA.

Antisense oligonucleotides in accordance with the present invention are selected such that the antisense sequence exhibits the least likelihood of forming duplexes, hairpins or dimers, and contains minimal or no homooligomer/sequence repeats. The oligonucleotide may further contain a GC clamp. One skilled in the art will appreciate that these properties can be determined qualitatively using various computer modelling programs, for example, the program OLIGO® Primer Analysis Software, Version 5.0 (distributed by National Biosciences, Inc., Plymouth, MN).

In order to be effective, conventional antisense oligonucleotides are typically less than about 100 nucleotides in length, for example, between 7 and 100 nucleotides in length. In one embodiment of the present invention, the antisense oligonucleotides are less than about 50 nucleotides in length, for example between about 7 and about 50 nucleotides in length. In another embodiment, the antisense oligonucleotides are between about 10 and about 50 nucleotides in length. In a further embodiment, the antisense oligonucleotides are between about 12 and about 50 nucleotides in length. In other embodiments, the antisense oligonucleotides are less than about 35 nucleotides in length, for example between about 7 and about 35 nucleotides in length, between about 10 and about 35 nucleotides, between about 12 and about 35 nucleotides, or between about 15 and 35 nucleotides. In other embodiments, the antisense oligonucleotides are less than about 30 nucleotides in length, for example between about 15 and 30 nucleotides, or between about 12 and 30 nucleotides. In other embodiments, the antisense oligonucleotides are less than about 25 nucleotides in length, for example, between about 15 and 25 nucleotides, and between about 12 and about 25 nucleotides in length.

TABLE 1

Target Sequences to POLE

| Name | Sequence |
| --- | --- |
| POLE-a (SEQ ID NO: 1) | 5'-GCGAGGAACAGGCGAAAUA-3' |
| POLE-b (SEQ ID NO: 2) | 5'-GGAGGAGGGUGCUUCGUAU-3' |
| POLE-c (SEQ ID NO: 3) | 5'-GGACAGGCGUUACGAGUUC-3' |
| POLE-d (SEQ ID NO: 4) | 5'-CUCGGAAGCUGGAAGAUUA-3' |
| POLE-e (SEQ ID NO: 5) | 5'-UCACGCAGUGAAUGCUUUUC-3' |
| POLE-f (SEQ ID NO: 6) | 5'-ACAGCCUCACAGGAGCAGUU-3' |
| POLE-g (SEQ ID NO: 7) | 5'-ACUGACCACCCUGACUGUCC-3' |
| POLE-h (SEQ ID NO: 8) | 5'-UUUUCAGGGAGCUCAGACGU-3' |

TABLE 2

Target Sequences to POLD1

| | Sequence |
| --- | --- |
| POLD1-a (SEQ ID NO: 9) | 5'-AGUUGGAGAUUGACCAUUA-3' |
| POLD1-b (SEQ ID NO: 10) | 5'-CGAGAGAGCAUGUUUGGGU-3' |

TABLE 2-continued

Target Sequences to POLD1

| | Sequence |
| --- | --- |
| POLD1-c (SEQ ID NO: 11) | 5'GCAAAGGCAUCUUCCCUGA 3' |
| POLD1-d (SEQ ID NO: 12) | 5'GCACAGAAACUGGGCCUGA 3' |
| POLD1-e (SEQ ID NO: 13) | 5'AGGAUGGAAGCGGGACCC 3' |

Examples of suitable target sequences within the MSH2 gene or mRNA for the design of antisense oligonucleotides are known in the art. For example, Dharmacon Inc. (Lafayette, CO) provides a number of siRNA sequences targeted to MSH2 gene that could serve as the basis for the design of antisense therapeutics. Examples of siRNA target sequences known in the art are provided in Table 3 below.

TABLE 3

Target Sequences to MSH2

| Name | Sequence |
| --- | --- |
| MSH2-a (SEQ ID NO: 14) | 5'-GCAGAUGAAUAGUGCUGUA-3' |
| MSH2-b (SEQ ID NO: 15) | 5'-GAAGAGACCUUAACUAUGC-3' |
| MSH2-c (SEQ ID NO: 16) | 5'-CAACAUAUAUUCGACAAAC-3' |
| MSH-d (SEQ ID NO: 17) | 5'-GAGAAUGAUUGGUAUUUGG-3' |

Examples of suitable target sequences within the MSH2 gene or mRNA for the design of antisense oligonucleotides are known in the art. For example, Dharmacon Inc. (Lafayette, CO) provides a number of siRNA sequences targeted to MSH2 gene that could serve as the basis for the design of antisense therapeutics.

TABLE 4

MLH1 Target Sequences

| Name | Sequence |
| --- | --- |
| MLH1-a (SEQ ID NO: 18) | 5'-GGAAGUUGUUGGCAGGUAU-3' |
| MLH1-b (SEQ ID NO: 19) | 5'-CCAGAUGGUUCGUACAGAU-3' |
| MLH-c (SEQ ID NO: 20) | 5'-GAAGUAGUGAUAAGGUCUA-3' |
| MLH-d (SEQ ID NO: 21) | 5'-UAUCUUCAUUCUUCGACUA-3' |
| MLH-e (SEQ ID NO: 22) | 5'-AUGCACUGUGGGAUGUGUUC-3' |

TABLE 5

PMS2 Target Sequences

| Name | Sequence |
|---|---|
| PMS2-a (SEQ ID NO: 23) | 5'-UAAUGAAGCUGUUCUGAUA-3' |
| PMS2-b (SEQ ID NO: 24) | 5'-UCUAUGAGUUCUUUAGCUA-3' |
| PMS2-c (SEQ ID NO: 25) | 5'-GGAUGUUGAAGGUAACUUA-3' |
| PMS2-d (SEQ ID NO: 26) | 5'-GGAAUAUUAAGAAGGAGUA-3' |

TABLE 6

MSH6 Target Sequences

| Name | Sequence |
|---|---|
| MSH6-a (SEQ ID NO: 27) | 5'-CGAAGUAGCCGCCAAAUAA-3' |
| MSH6-b (SEQ ID NO: 28) | 5'-CCACAUGGAUGCUCUUAUU-3' |
| MSH6-c (SEQ ID NO: 29) | 5'-GCAGAAGGGCUAUAAAGUA-3' |
| MSH6-d (SEQ ID NO: 30) | 5'-GGGCCAAGAUGGAGGGUUA-3' |

It is understood in the art that an antisense oligonucleotide need not have 100% identity with the complement of its target sequence. The antisense oligonucleotides in accordance with the present invention have a sequence that is at least about 75% identical to the complement of their target sequence. In one embodiment of the present invention, the antisense oligonucleotides have a sequence that is at least about 90% identical to the complement of the target sequence. In another embodiment, they have a sequence that is at least about 95% identical to the complement of target sequence, allowing for gaps or mismatches of several bases. In a further embodiment, they are at least about 98% identical to the complement of the target sequence. Identity can be determined, for example, by using the BLASTN program of the University of Wisconsin Computer Group (GCG) software or provided on the NCBI website.

In one embodiment, the antisense therapeutic is capable of decreasing or ablating the expression of the mismatch repair gene to which it is targeted. Methods of determining the ability of antisense therapeutic to decrease expression of a target gene are well-known in the art and may determine the decrease in expression at the nucleic acid level or the protein level or both. For example, after incubation of cells from an appropriate cell line with the antisense therapeutic, the expression of the mismatch repair enzyme mRNA or protein can be determined using standard techniques known in the art. Numerous techniques are known to the skilled worker, including DNA arrays, microarrays, protein arrays, proteomics, Northern blots, RT-PCR analysis, Western blot, and the like.

In the context of this invention, an oligonucleotide (OLIGO) can be an oligomer or polymer of ribonucleic acid (RNA), deoxyribonucleic acid (DNA), or modified RNA or DNA, or combinations thereof. This term, therefore, includes oligonucleotides composed of naturally-occurring nucleobases, sugars and covalent internucleoside (backbone) linkages as well as oligonucleotides having non-naturally-occurring portions, which function similarly. Such modified oligonucleotides are often preferred over native forms because of desirable properties such as, for example, enhanced cellular uptake, enhanced affinity for nucleic acid target and increased stability in the presence of nucleases. In one embodiment of the present invention, the antisense oligonucleotides comprise DNA and/or modified DNA. In another embodiment, the antisense oligonucleotides comprise RNA and/or modified RNA. In another embodiment, the antisense oligonucleotides comprise both DNA and RNA, and/or modified versions thereof.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific non-limiting examples of modified oligonucleotides useful in the present invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary antisense oligonucleotides having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In one embodiment of the present invention, the antisense oligonucleotide is a phosphorothioated oligonucleotide that comprises one or more phosphorothioate internucleotide linkages. In another embodiment, the antisense oligonucleotide comprises phosphorothioate internucleotide linkages that link the four, five or six 3'-terminal nucleotides of the oligonucleotide. In a further embodiment, the antisense oligonucleotide comprises phosphorothioate internucleotide linkages that link all the nucleotides of the oligonucleotide.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene-containing backbones; sulphamate backbones; methyleneimino and methylenehydrazino backbones; sulphonate and sulfonamide backbones; amide backbones; and others having mixed N, O, S and CH$_2$ component parts.

The present invention also contemplates modified oligonucleotides in which both the sugar and the internucleoside linkage of the nucleotide units are replaced with novel groups. The base units are maintained for hybridization with an appropriate nucleic acid target compound. An example of such a modified oligonucleotide, which has been shown to have excellent hybridization properties, is a peptide nucleic acid (PNA) [Nielsen et al., *Science*, 254:1497-1500 (1991)]. In PNA compounds, the sugar-backbone of an oligonucleotide is replaced with an amide-containing backbone, in particular an aminoethylglycine backbone. The nucleobases are retained and are bound directly or indirectly to aza-nitrogen atoms of the amide portion of the backbone.

The present invention also contemplates oligonucleotides comprising "locked nucleic acids" (LNAs), which are conformationally restricted oligonucleotide analogues containing a methylene bridge that connects the 2'-0 of ribose with the 4'-C (see, Singh et al., *Chem. Commun.*, 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron*, 1998, 54:3607-3630). Studies of mis-matched sequences show that LNA obey the Watson-Crick base pairing rules with generally improved selectivity compared to the corresponding unmodified reference strands.

Antisense oligonucleotides containing LNAs have been demonstrated to be efficacious and non-toxic (Wahlestedt et al., *Proc. Natl. Acad. Sci. U.S.A.*, 2000, 97:5633-5638). In addition, the LNA/DNA copolymers were not degraded readily in blood serum and cell extracts.

LNAs form duplexes with complementary DNA or RNA or with complementary LNA, with high thermal affinities. The universality of LNA-mediated hybridization has been emphasized by the formation of exceedingly stable LNA: LNA duplexes (Koshkin et al., *J. Am. Chem. Soc.*, 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., *J. Org. Chem.*, 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.*, 1998, 8:2219-2222).

Modified oligonucleotides may also contain one or more substituted sugar moieties. For example, oligonucleotides may comprise sugars with one of the following substituents at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Examples of such groups are: O[(CH$_2$)$_n$O], CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Alternatively, the oligonucleotides may comprise one of the following substituents at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—CH$_2$ CH$_2$ OCH$_3$, also known as 2'-O-(2-methoxyethyl) or 2'-MOE) [Martin et al., *Helv. Chim. Acta*, 78:486-504 (1995)], 2'-dimethylaminooxyethoxy (O(CH$_2$)$_2$ ON(CH$_3$)$_2$ group, also known as 2'-DMAOE), 2'-methoxy (2'-O—CH$_3$), 2'-aminopropoxy (2'-OCH$_2$ CH$_2$ CH$_2$ NH$_2$) and 2'-fluoro (2'-F).

In one embodiment of the present invention, the antisense oligonucleotide comprises at least one nucleotide comprising a substituted sugar moiety. In another embodiment, the antisense oligonucleotide comprises at least one 2'-O-(2-methoxyethyl) or 2'-MOE modified nucleotide. In another embodiment, the antisense oligonucleotide comprises at least one 2'-0-methyl or 2'-MOE ribonucleotide.

Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include modifications to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte Chemie, Int. Ed.*, 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications, pp 276-278*, Crooke, S. T. and Lebleu, B., ed., CRC Press, Boca Raton].

Another oligonucleotide modification included in the present invention is the chemical linkage to the oligonucleotide of one or more moieties or conjugates which enhance the activity, cellular distribution or cellular uptake of the oligonucleotide. Such moieties include, but are not limited to, lipid moieties such as a cholesterol moiety [Letsinger et al., *Proc. Natl. Acad. Sci. USA,* 86:6553-6556 (1989)], cholic acid [Manoharan et al., *Bioorg. Med. Chem. Let.,* 4:1053-1060 (1994)], a thioether, e.g. hexyl-S-tritylthiol [Manoharan et al., *Ann. N.Y. Acad. Sci.,* 660:306-309 (1992); Manoharan et al., *Bioorg. Med. Chem. Lett.,* 3:2765-2770 (1993)], a thiocholesterol [Oberhauser et al., *Nucl. Acids Res.,* 20:533-538 (1992)], an aliphatic chain, e.g. dodecandiol or undecyl residues [Saison-Behmoaras et al., *EMBO J.,* 10:1111-1118 (1991); Kabanov et al., *FEBS Lett.,* 259:327-330 (1990); Svinarchuk et al., *Biochimie,* 75:49-54 (1993)], a phospholipid, e.g. di-hexadecyl-rac-glycerol or triethyl-ammonium 1,2-di-O-hexadecyl-rac-glycero-3-H-phosphonate [Manoharan et al., *Tetrahedron Lett.,* 36:3651-3654 (1995); Shea et al., *Nucl. Acids Res.,* 18:3777-3783 (1990)], a polyamine or a polyethylene glycol chain [Manoharan et al., *Nucleosides & Nucleotides,* 14:969-973 (1995)], or adamantane acetic acid [Manoharan et al., *Tetrahedron Lett.,* 36:3651-3654 (1995)], a palmityl moiety [Mishra et al., *Biochim. Biophys. Acta,* 1264:229-237 (1995)], or an octadecylamine or hexylamino-carbonyl-oxycholesterol moiety [Crooke et al., *J. Pharmacol. Exp. Ther.,* 277:923-937 (1996)].

One skilled in the art will recognize that it is not necessary for all positions in a given oligonucleotide to be uniformly modified. The present invention, therefore, contemplates the incorporation of more than one of the aforementioned modifications into a single oligonucleotide or even at a single nucleoside within the oligonucleotide.

In one embodiment of the present invention, the antisense oligonucleotides are gapmers. As used herein, the term "gapmer" refers to an antisense oligonucleotide comprising a central region (a "gap") and a region on either side of the central region (the "wings"), wherein the gap comprises at least one modification difference compared to each wing. Such modifications include nucleotide, internucleoside linkage, and sugar modifications as well as the absence of modification (unmodified RNA or DNA). Thus, in certain embodiments, the nucleotide linkages in each of the wings are different from the nucleotide linkages in the gap. In certain embodiments, each wing comprises modified nucleotides and the gap comprises nucleotides that do not comprise that modification. In certain embodiments the nucleotides in the gap and the nucleotides in the wings all comprise modified nucleotides, but the modifications in the gap are different from the modifications in each of the wings. In certain embodiments, the modifications in the wings are the same as one another. In certain embodiments, the modifications in the wings are different from each other. In certain embodiments, nucleotides in the gap are unmodified and nucleotides in the wings are modified. In certain embodiments, the modification(s) within each wing are the same. In certain embodiments, the modification(s) in one wing are different from the modification(s) in the other wing. In certain embodiments, the nucleotide linkages are the same in the gap and in the wings, but the wings comprise modified nucleotides whereas the gap does not. In one embodiment, the nucleotides in the wings comprise 2'-MOE modifications and the nucleotides in the gap do not.

Figure 7:
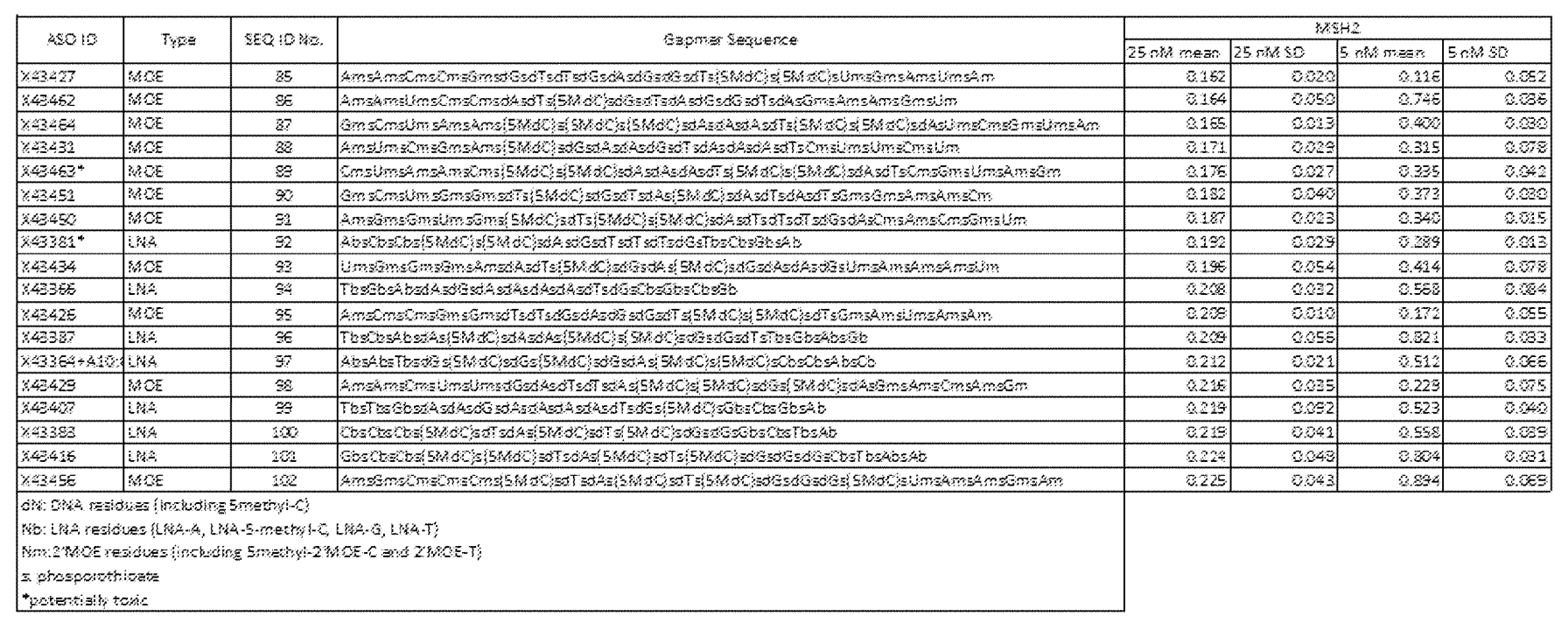

Examples of suitable gapmers targeting the MSH2 gene are shown in the table below and in FIG. 7. Preferred gapmers are shown in FIG. 5*b*.

TABLE 7

MSH2 gapmers

| ASO ID | Type | Gapmer Sequence |
|---|---|---|
| X43415 | LNA | AbsTbsAbs(5MdC)s(5MdC)s(5MdC)sdTsdGsdAsdTsdAsdGsdAsGbsTbsCbsGb |
| X43412 | LNA | GbsTbsCbsdGsdGsdTsdTsdAsdAsdGsdAsdTs(5MdC)sTbsGbsGbsGb |
| X43410 | LNA | AbsTbsCbsdGsdAs(5MdC)sdGsdAsdAsdGsdTsdAsdAsAbsTbsCbsTb |
| X43411 | LNA | GbsGbsGbsdAsdAsdTs(5MdC)sdGsdAs(5MdC)sdGsdAsdAsGbsTbsAbsAb |
| X43414 | LNA | TbsAbsCbs(5MdC)s(5MdC)sdTsdGsdAsdTsdAsdGsdAsdGsTbsCbsGbsGb |
| X43423 | MOE | GmsGmsCmsCmsAmsdTs(5MdC)sdAsdAs(5MdC)sdTsdGs(5MdC)sdGsdGsAmsCmsAmsUmsUm |
| X43409 | LNA | TbsCbsGbsdAs(5MdC)sdGsdAsdAsdGsdTsdAsdAsdAsTbsCbsTbsTb |
| X43413 | LNA | AbsAbsGbsdTs(5MdC)sdGsdGsdTsdTsdAsdAsdGsdAsTbsCbsTbsGb |
| X43395 | LNA | CbsCbsCbsdTsdGsdAsdTsAsdGsdAsdGsdTsCbsGbsGbsTb |
| X43370 | LNA | GbsGbsGbsdAsdAsdTs(5MdC)sdGsdAs(5MdC)sdGsAbsAbsGbsTb |
| X43371 | LNA | GbsTbsCbsdGsdGsdTsdTsdAsdAsdGsdAsTbsCbsTbsGb |
| X43369 | LNA | AbsTbsCbsdGsdAs(5MdC)sdGsdAsdAsdGsdTsAbsAbsAbsTb |
| X43408 | LNA | CbsTbsCbsdTsdAsdTsdAs(5MdC)sdTsdGsdAs(5MdC)sdGsAbsAbsCbsCb |
| X43368 | LNA | TbsCbsGbsdAs(5MdC)sdGsdAsdAsdGsdTsdAsAbsAbsTbsCb |
| X43372 | LNA | AbsGbsTbs(5MdC)sdGsdGsdTsdTsdAsdAsdGsAbsTbsCbsTb |
| X43425 | MOE | CmsCmsGmsGmsUmsdTsdGsdAsdGsdGsdTs(5MdC)s(5MdC)sdTsdGsAmsUmsAmsAmsAm |

TABLE 7-continued

MSH2 gapmers

| ASO ID | Type | Gapmer Sequence |
|---|---|---|
| X43442 | MOE | AmsAmsAmsCmsUmsdTs<br>(5MdC)sdTsdTsdGsdGs<br>(5MdC)sdAsdAsdGsUms<br>CmsGmsGmsUm |
| X43380 | LNA | GbsTbsAbsdTsdAs(5MdC)<br>sdGsdTs(5MdC)sdAsdTs<br>TbsAbsGbsGb | dN: DNA residues (including 5methyl-C)
Nb: LNA residues (LNA-A, LNA-5-methyl-C, LNA-G, LNA-T)
Nm: 2'-MOE residues (including 5methyl-2'-MOE-C and 2'-MOE-T)
s: phosphorothioate In the context of the present invention, an antisense oligonucleotide is "nuclease resistant" when it has either been modified such that it is not susceptible to degradation by DNA and RNA nucleases or alternatively has been placed in a delivery vehicle which in itself protects the oligonucleotide from DNA or RNA nucleases. Nuclease-resistant oligonucleotides include, for example, methyl phosphonates, phosphorothioates, phosphorodithioates, phosphotriesters, and morpholino oligomers. Suitable delivery vehicles for conferring nuclease resistance include, for example, liposomes. In one embodiment of the present invention, the antisense oligonucleotides are nuclease-resistant.

In some embodiments of the present invention, the antisense sequences may be provided in the context of RNAi constructs comprising sequences specific for mismatch repair protein In one embodiment of the present invention, the RNAi construct comprises a single-stranded polynucleotide that forms a hairpin structure which includes a double-stranded stem and a single-stranded loop, wherein the double-stranded stem can be cleaved by Dicer to produce an siRNA.

In one embodiment, the RNAi construct comprises a double-stranded (dsRNA) construct. The RNAi constructs may be modified to increase stability or increase cellular uptake.

The present invention further contemplates antisense oligonucleotides that contain groups for improving the pharmacokinetic properties of the oligonucleotide, or groups for improving the pharmacodynamic properties of the oligonucleotide.

In embodiments of the present invention where antisense oligonucleotides directed to nucleic acids encoding two or more target proteins are used, each oligonucleotide may be independently modified.

In one embodiment of the present invention, shRNA are used.

In one embodiment of the present invention, siRNA are used.

Appropriate CRISPR methods and vectors are known in the art and include those described in US20160324987; WO2015139139 and WO2015089419. In some embodiments, the CRISPR method is used to introduce missense mutations into POLD1, POLE1 or both POLD1 and POLE1 to reduce DNA polymerase proofreading.

Pharmaceutical Compositions

The antisense therapeutics may be administered as a pharmaceutical composition in which the antisense therapeutics are admixed with an appropriate pharmaceutically acceptable carrier, diluent, excipient or vehicle.

The pharmaceutical compositions of the present invention may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques, including and especially into body cavities and compartments such as the central nervous system, the peritoneum, the pleura and pericardium, the liver, and isolated limbs.

The present invention also provides for pharmaceutical compositions comprising an antisense oligonucleotide associated with a liposomal-type vehicle, such as an artificial membrane vesicle (including a liposome, lipid micelle and the like), microparticle or microcapsule.

The pharmaceutical compositions may be in a form suitable for oral use, for example, as tablets, troches, lozenges, aqueous or oily suspensions, dispersible powders or granules, emulsion hard or soft capsules, or syrups or elixirs. Compositions intended for oral use may be prepared according to methods known to the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed.

Pharmaceutical compositions for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Aqueous suspensions contain the active compound in admixture with suitable excipients including, for example, suspending agents, such as sodium carboxymethylcellulose, methyl cellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxybenzoate, one or more colouring agents, one or more flavouring agents or one or more sweetening agents, such as sucrose or saccharin.

Oily suspensions may be formulated by suspending the active ingredients in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example, olive oil or arachis oil, or a mineral oil, for example, liquid paraffin, or it may be a mixture of these oils. Suitable emulsifying agents may be naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative, and/or flavouring and colouring agents.

The pharmaceutical compositions may be in the form of a sterile injectable aqueous or oleaginous suspension. This suspension may be formulated according to known art using suitable dispersing or wetting agents and suspending agents such as those mentioned above. The sterile injectable preparation may also be sterile injectable solution or suspension in a non-toxic parentally acceptable diluent or solvent, for example, as a solution in 1,3-butanediol. Acceptable vehicles and solvents that may be employed include, but are not limited to, water, Ringers solution, lactated Ringer's solution and isotonic sodium chloride solution. Other examples are, sterile, fixed oils which are conventionally employed as a solvent or suspending medium, and a variety of bland fixed oils including, for example, synthetic mono- or diglycerides. In addition, fatty acids such as oleic acid find use in the preparation of injectables.

In one embodiment of the present invention, the pharmaceutical composition comprising the antisense oligonucleotide is formulated for injection or infusion.

Other pharmaceutical compositions and methods of preparing pharmaceutical compositions are known in the art and are described, for example, in "*Remington: The Science and Practice of Pharmacy,*" Gennaro, A., Lippincott, Williams & Wilkins, Philadelphia, PA (2000) (formerly "Remingtons Pharmaceutical Sciences").

In some embodiments, the therapeutic is formulated for regional perfusion including intraperitoneal perfusion, intrapleural perfusion, hepatic perfusion, and installation into the central nervous system such as by lumbar puncture, intra- or transnasally or catheter into cerebrospinal fluid.

Use of the Antisense Therapeutics

The present invention provides for the use of the antisense therapeutics in the treatment of cancer. The antisense therapeutics may be used alone as single agents or may be used in combination with another cancer therapy. When used as a single agent, the antisense therapeutics may be used singly or in tandem (i.e. two antisense therapeutic targeting the same mRNA), or the antisense therapeutics may be combined in various other ways (for example, three or more antisense oligonucleotides targeting the same DNA mismatch repair protein gene or DNA polymerase protein or mRNA, or two or more two antisense oligonucleotides each targeting a different DNA mismatch repair protein gene or DNA polymerase or mRNA). In some embodiments, the antisense therapeutics targeting DNA mismatch repair protein gene are used in conjunction with other antisense therapeutics targeting other genes including DNA polymerases; or used together in different embodiments such as siRNA together with an oligonucleotide against the same or a different target.

The present invention contemplates the use of the antisense therapeutics in the treatment of a variety of cancers. Treatment of cancer encompasses the use of the antisense oligonucleotides to treat, stabilize or prevent cancer. In this context, treatment with the antisense oligonucleotides may result in, for example, a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptom associated with a tumor, a slowing of tumor regression, or an increase in the overall survival time of a subject having cancer.

Examples of cancers which may be may be treated or stabilized in accordance with the present invention include, but are not limited to haematologic neoplasms, including leukaemias and lymphomas; carcinomas, including adenocarcinomas; melanomas and sarcomas. Carcinomas, adenocarcinomas and sarcomas are also frequently referred to as "solid tumors." Examples of commonly occurring solid tumors include, but are not limited to, cancer of the brain (including anaplastic astrocytoma and glioblastoma multiforme), breast, cervix, colon, rectum, head and neck, kidney, lung including both small cell and non-small cell lung cancer, ovary, pancreas, prostate, stomach and uterus. Various forms of lymphoma also may result in the formation of a solid tumor and, therefore, in certain contexts may also be considered to be solid tumors.

Examples of cancer can include colorectal cancer and in particular colorectal cancer that is not defective in mismatch repair; or for use in mismatch defective colorectal cancer with antisense against a polymerase target.

In some embodiments, the cancer is a cancer with a low TMB.

The term "leukaemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "lymphoma" generally refers to a malignant neoplasm of the lymphatic system, including cancer of the lymphatic system. The two main types of lymphoma are Hodgkin's disease (HD or HL) and non-Hodgkin's lymphoma (NHL). Abnormal cells appear as congregations which enlarge the lymph nodes, form solid tumors in the body, or more rarely, like leukemia, circulate in the blood. Hodgkins' disease lymphomas include: nodular lymphocyte predominance Hodgkin's lymphoma; classical Hodgkin's lymphoma; nodular sclerosis Hodgkin's lymphoma; lymphocyte-rich classical Hodgkin's lymphoma; mixed cellularity Hodgkin's lymphoma; lymphocyte depletion Hodgkin's lymphoma. Non-Hodgkin's lymphomas include small lymphocytic NHL; follicular NHL; mantle cell NHL; mucosa-associated lymphoid tissue (MALT) NHL; diffuse large cell B-cell NHL; mediastinal large B-cell NHL; precursor T lymphoblastic NHL; cutaneous T-cell NHL; T-cell and natural killer cell NHL; mature (peripheral) T-cell NHL; Burkitt's lymphoma; mycosis fungoides; Sézary Syndrome; precursor B-lymphoblastic lymphoma; B-cell small lymphocytic lymphoma; lymphoplasmacytic lymphoma; splenic marginal zone B-cell lymphoma; nodal marginal zone lymphoma; plasma cell myeloma/plasmacytoma; intravascular large B-cell NHL; primary effusion lymphoma; blastic natural killer cell lymphoma; enteropathy-type T-cell lymphoma; hepatosplenic gamma-delta T-cell lymphoma; subcutaneous panniculitis-like T-cell lymphoma; angioimmunoblastic T-cell lymphoma; and primary systemic anaplastic large T/null cell lymphoma.

The term "sarcoma" generally refers to a tumor which originates in connective tissue, such as muscle, bone, cartilage or fat, and is made up of a substance like embryonic connective tissue and is generally composed of closely packed cells embedded in a fibrillar or homogeneous substance. Sarcomas include soft tissue sarcomas, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, choriocarcinoma, embryonal sarcoma, Wilms tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented haemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, sublingual melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colorectal carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epidermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, lipomatous carcinoma, lymphoepithelial carcinoma, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, non-small cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia. Examples include, but are not limited to, adenocarcinomas of the breast, lung, pancreas and prostate.

Additional cancers encompassed by the present invention include, for example, multiple myeloma, neuroblastoma, rhabdomyosarcoma, primary thrombocytosis, primary macroglobulinemia, small-cell lung tumors, primary brain tumors, malignant pancreatic insulinoma, malignant carcinoid, urinary bladder cancer, premalignant skin lesions, gliomas, testicular cancer, thyroid cancer, esophageal cancer, genitourinary tract cancer, malignant hypercalcemia, endometrial cancer, adrenal cortical cancer, mesothelioma and medulloblastoma.

Antisense oligonucleotides are typically administered parenterally, for example, by intravenous infusion. Other methods of administering antisense oligonucleotides are known in the art.

Combination Therapies

In one embodiment, the present invention provides for the use of the antisense therapeutics in the treatment of cancer in combination with other cancer therapies, such as immunotherapy, radiation therapy or chemotherapy.

Appropriate immunotherapies include anti-CTLA-4 therapeutics such as Ipilimumab, anti-PD-1 inhibitors including Nivolumab, Pembrolizumab, and Spartalizumab and PD-L1 inhibitors such as Atezolizumab, Avelumab and Durvalumab; and other checkpoint inhibitors.

To gain a better understanding of the invention described herein, the following examples are set forth. It will be understood that these examples are intended to describe illustrative embodiments of the invention and are not intended to limit the scope of the invention in any way.

EXAMPLES

Down-Regulation of mRNA Expression with siRNA siRNAs used for this experiment were obtained from ThermoFisher (Dharmacon). A control siRNA was provided, the sequence of which does not align with any known RNA sequence. This is referred to as sc-2. One siRNA was tested against each of 6 gene products: MLH1, MSH2, polE, PMS2, MSH6, and PolD1. Cell lines were cultured in alpha Minimum Essential Medium (aMEM) plus 10% fetal bovine serum with penicillin-streptomycin (growth medium) at 37° C. in a humidified atmosphere of 5% $CO_2$. Rapidly proliferating, cultured cells were harvested by trypsinization and re-plated into 25-cm$^2$ flasks at a density of 30,000 to 50,000 cells per flask, depending on the cell line. After 24 hours, to allow cells to plate and condition the medium, cells were exposed to siRNA as follows: siRNA was diluted in aMEM (serum-free) with Lipofectamine 2000 (LFA2K) [5× the desired final concentration, therefore 25 nM in 3.125 μg/ml LFA2K], and incubated at room temperature for 20 minutes. This solution was then applied to cultured cells (0.2× volume into 2 ml of medium in flask), yielding a final concentration of 5 nM for each siRNA, and incubated at 37° C. for 4 hours. One experiment also included the combination of 5 nM of each of MLH1 and polE. After the 4-hour incubation, 5 ml of growth medium were applied to flasks, and then incubated for another 20 h. Following this incubation, cells were harvested by scraping in lysis buffer as provided in the Qiagen RNeasy isolation kit, and total RNA was obtained using the RNeasy columns according to manufacturer's instructions. Samples of total RNA were sent to the Genetic Analysis Facility, The Centre for Applied Genomics, The Hospital for Sick Children for analysis of relative expression of targeted gene products.

Results

Shown in the table below are the target mRNA sequences and the corresponding siRNA sequences, used in qRT-PCR experiments. Down-regulation of the target mRNA compared scramble siRNA control is shown. Results were normalized to GAPDH control.

| Target mRNA seq | siRNA | siRNA seq | qRT-PCR level compared to control | |
|---|---|---|---|---|
| 5'-GAAGUUGUU GGCAGGUAU-3' | MLH1-a | 5'-atacctgcca acaacttcc-3' | 50% 43% | 5 nM 10 nM |
| 5'-CCAGAUGGU UCGUACAGAU-3' | MLH1-b | 5'-atctgtacga accatctgg-3' | 50% 43% | 5 nM 10 nM |
| 5'-UAUCUUCAU UCUUCGACUA-3' | MLH1-d | 5'-tagtcgaaga atgaagata-3' | 58% 40% | 5 nM 10 nM |
| 5'-GCAGAUGAA UAGUGCUGUA-3' | MSH2-a | 5'-tacagcacta ttcatctgc-3' | 32% | 5 nM |
| 5'-GAAGAGACC UUAACUAUGC-3' | MSH2-b | 5'-gcatagttaa ggtctcttc-3' | 34% | 5 nM |
| 5'-GAGAAUGAU UGGUAUUUGG-3' | MSH2-d | 5'-ccaaatacca atcattctc-3' | 40% | 5 nM |
| 5'-CGAAGUAGC CGCCAAAUAA-3' | MSH6-a | 5'-ttatttggcg gctacttcg-3' | 25% | 5 nM |
| 5'-GGGCCAAGA UGGAGGGUUA-3' | MSH6-d | 5'-taaccctcc atcttggccc-3' | 28% | 5 nM |
| 5'-CCACAUGGA UGCUCUUAUU-3' | MSH6-b | 5'-ttattgagca tccatgtgg-3' | 38% | 5 nM |
| 5'-GGAUGUUGA AGGUAACUUA-3' | PMS2-c | 5'-taagttacct tcaacatcc-3' | 36% | 5 nM |
| 5'-UCUAUGAGU UCUUUAGCUA-3' | PMS-b | 5'-tagctaaaga actcataga-3' | 40% | 5 nM |
| 5'-GGAAUAUUA AGAAGGAGUA-3' | PMS2-d | 5'-tactccttc ttaatattcc-3' | 42% | 5 nM |
| 5'-UAAUGAAGC UGUUCUGAUA-3' | PMS2-a | 5'-tatcagaac agcttcatta-3' | 44% | 5 nM |
| 5'-GCGAGGAAC AGGCGAAAUA-3' | POLE-a | 5'-tatttcgcc tgttcctcgc-3' | 61% 48% | 5 nM 10 nM |
| 5'-GGAGGAGGG UGCUUCGUAU-3' | POLE-b | 5'-atacgaagc accctcctcc-3' | 70% 52% | 5 nM 10 nM |
| 5'-CUCGGAAGC UGGAAGAUUA-3' | POLE-d | 5'-taatcttcc agcttccgag-3' | 90% 50% | 5 nM 10 nM |
| 5'-CGAGAGAGC AUGUUUGGGU-3' | POLD1-b | 5'-acccaaaca tgctctctcg-3' | 35% | 5 nM |
| 5'-AGUUGGAGA UUGACCAUUA-3' | POLD1-a | 5'-taatggtca atctccaact-3' | 37% | 5 nM |

Figure 3:
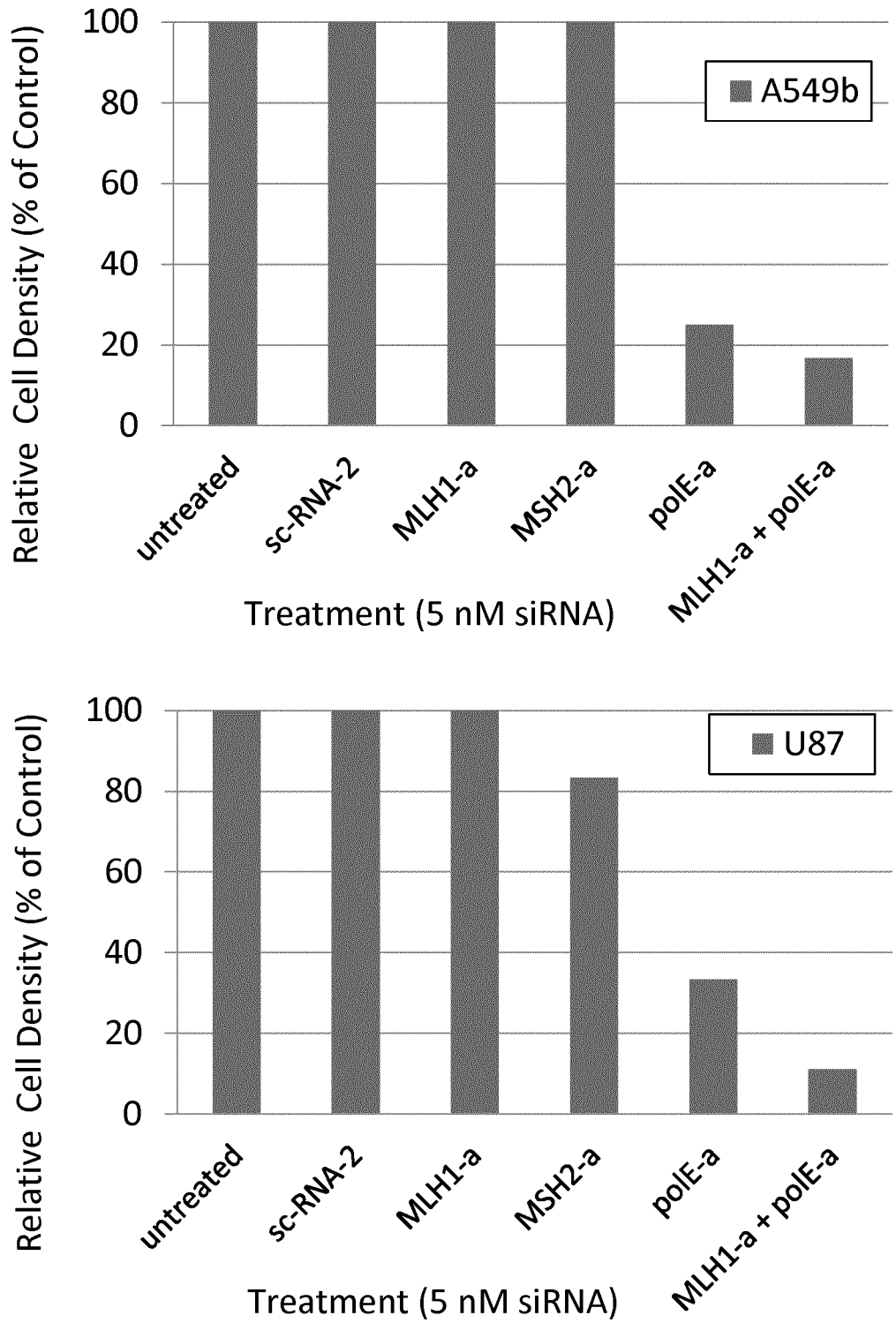
FIG. 3 details impact of siRNA on relative cell density of A549b and U87 cells.

Referring to FIGS. 3 and 4, transfection of A549b lung cells and U87 glioma cells with siRNA targeting polε alone or in combination with siRNA targeting MLH1 is antiproliferative and/or toxic as evidenced by the reduction in cell density and DNA content which may be the result of a level of genome instability that is incompatible with viability.

Tumor Mutation Burden (TMB) siRNAs used for this experiment was obtained from ThermoFisher (Dharmacon). A control siRNA was provided, the sequence of which does not align with any known RNA sequence. This is referred to as sc-2. One siRNA was tested against each of 3 gene products: MLH1, MSH2, polE, plus the combination of MLH1 and polE.

Cell lines were cultured in alpha Minimum Essential Medium (aMEM) plus 10% fetal bovine serum with penicillin-streptomycin (growth medium) at 37° C. in a humidified atmosphere of 5% $CO_2$. Rapidly proliferating, cultured cells were harvested by trypsinization and replated into 25-$cm^2$ flasks at a density of 30,000 to 50,000 cells per flask, depending on the cell line. After 24 hours, to allow cells to plate and condition the medium, cells were exposed to siRNA as follows: siRNA was diluted in aMEM (serum-free) with Lipofectamine 2000 (LFA2K) [5× the desired final concentration, therefore 25 nM in 3.125 µg/ml LFA2K], and incubated at room temperature for 20 minutes. This solution was then applied to cultured cells (0.2× volume into 2 ml of medium in flask), yielding a final concentration of 5 nM for each siRNA, plus the combination of 5 nM of each of MLH1 and polE, and incubated at 37° C. for 4 hours. At this time, 5 ml of growth medium were applied to flasks, and then incubated for another 5 days. Following this incubation, cells were harvested by scraping in lysis buffer as provided in the Qiagen DNeasy isolation kit, and total DNA was obtained using the DNeasy columns according to manufacturer's instructions. Samples of total DNA were delivered to the London Regional Genomics Centre, Robarts Research Institute, University of Western Ontario (David Carter, Facility Manager) for sequencing, to determine TMB.

Illumina NextSeq Next Generation Sequencing

All samples were sequenced at the London Regional Genomics Centre (Robarts Research Institute, London, Ontario, Canada; http://www.lrgc.ca) using the Illumina NextSeq 500 (Illumina Inc., San Diego, CA).

DNA samples were quantified using the Qubit 2.0 Fluorometer (Thermo Fisher Scientific, Waltham, MA) and were processed using the Nextera DNA Exome kit from Illumina (Illumina Inc., San Diego, CA), following the manufacture's protocol.

Briefly, samples were fragmented, amplified with indexed primers, underwent two capture probe hybridizations, a bead clean-up and quantitated via the Qubit. After equimolar pooling, the library size distribution was assessed using the Agilent 2100 Bioanalyzer (Agilent Technologies Inc., Palo Alto, CA) and the DNA High Sensitivity DNA kit (Caliper Life Sciences, Mountain View, CA).

The library was sequenced as a paired end 2×150 bp run, using both a High Output v2 kit (300 cycles) and a Mid Output kit. Fastq data files were uploaded to BaseSpace for data analysis.

The fastq files were analyzed in BaseSpace using the BWA Enrichment software, v2.1.2 (Illumina Inc, San Diego, CA) for alignment to hg19. (https://support.illumina.com/help/BS App enr BWA help v2 1/BWAEnrichmentHelp.htm) Variant calling was done using BWA-MEM Genome Alignment Software and the GATK Variant Caller. The vcf files were run through the Variant Call Assessment Tool, v3.0.0 (Illumina Inc, San Diego, CA) to create pairwise comparisons, SNV (dbSNP build 147) and indel statistics. The vcf files were all annotated by the EDGC Annotator v 1.0.0 (EONE-DIAGNOMICS Genome Center, San Diego, CA) http://www.edac.com/ena/bbs/content.php?co id=research1), which includes data from ClinVar, OMIM, COSMIC, 1000 Genome Project allele frequencies, dbSNP and VEP (Variant Effect Predictor).

Results

FIGS. 6A to 6D show the impact of downregulation of mismatch repair and/or polymerase proofreading in four distinct cancer cell lines. Of particular interest is the impact of downregulation on the insertion and deletions (i.e. indels) mutations which are known the art to be the most immunogenic alterations because of their frameshift nature. A single indel mutation can create a novel open reading frame and thus has the potential to create a large number of neo-antigens. In particular, high rates of indel mutations are known in the art to trigger a greater abundance of neoantigens and increase the sensitivity to immune checkpoint inhibitors (Turajlic et al., Lancet Oncol 2017: 18: 1009-21) in a manner that is not necessarily reflected, and may be under-represented, in the total TMB score. Turajlic et al. suggests that the number of indels (i.e. indel load) more strongly correlates with sensitivity of immune checkpoint inhibitors than single nucleotide variations.

Assessment of the downregulation of both MMR and POLE is impacted by the anti-proliferative or toxic effect of the combination.

Shown in FIG. 6A are U87 glioblastoma cell line alterations (brain cancer) caused by MMR and POLE downregulation by siRNA. Downregulation caused a notable increase in the insertions and deletions (i.e. indels). In particular, downregulation of MLH1 resulted in 32 more insertions than scrambled control; downregulation of MSH2 resulted in 58 more insertions and 31 more deletions than scrambled control; downregulation of POLE resulted in 46 more insertions and 48 more deletions than scrambled control. Downregulation of both MLH1 and POLE caused 55 more insertions and 7 more deletions than scrambled control. Assessment of the downregulation of both MLH1 and POLE is impacted by the anti-proliferative or toxic effect of the combination.

Shown in FIG. 6B are A549 lung cancer cell line alterations caused by MMR and POLE downregulation by siRNA. Downregulation caused an increase in the insertions and deletions (i.e. indels). In particular, downregulation of MLH1 resulted in 67 more insertions and 44 more deletions than scrambled control; downregulation of MSH2 resulted in 31 more insertions and 4 more deletions than scrambled control; downregulation of POLE resulted in 20 more insertions and 59 more deletions than scrambled control. Assessment of the downregulation of both MLH1 and POLE is impacted by the anti-proliferative or toxic effect of the combination.

Shown in FIG. 6C are SK-MEL-5 melanoma cell line alterations caused by MMR and POLE downregulation by siRNA. Downregulation caused an increase in the insertions and deletions (i.e. indels). In particular, downregulation of MLH1 resulted in 23 more insertion and 71 more deletions than scrambled control; downregulation of MSH2 resulted in 12 more insertions and 42 more deletions than scrambled control; downregulation of POLE resulted in 12 more insertion and 17 deletions than scrambled control. Assessment of the downregulation of both MLH1 and POLE is impacted by the anti-proliferative or toxic effect of the combination.

Shown in FIG. 6D are HT-29 colon cancer cell line alterations caused by MMR and polymerase proofreading activity. Downregulation of PMS2 or MLH1 caused an increase in indels. Downregulation of both POLE and POLD again increased indels. In particular, downregulation of PMS2 resulted in 75 more insertions and 34 more deletions than scrambled control; downregulation of POLD1 resulted in 18 more insertions than scrambled control; downregulation of POLE resulted in 24 more insertions. Downregulation of POLE and POLD1 resulted in 41 more insertions and 12 more deletions than scrambled control.

A further analysis of the indel data for the A549 cells shows that the indels resulted in an increase in frameshift mutations. In particular, the combination of MLH1 and POLE downregulation generated an additional 23 frameshifts over control; MLH1 downregulation generated an additional 10 frameshifts over control; POLE downregulation generated an additional 6 frameshifts over control; and that this does suggest synergy in frameshift variant generation as a result of the combination (despite also being anti-proliferative).

The overall increase in indels and resulting frameshifts caused by downregulation of MMR and/or polymerase proofreading appears to be sufficient, if reflected in vivo, to convert immune checkpoint inhibitor non-responders to responders regardless of the impact on SNV.

Downregulation of MSH-2 mRNA using Gapmers

Figure 5A:
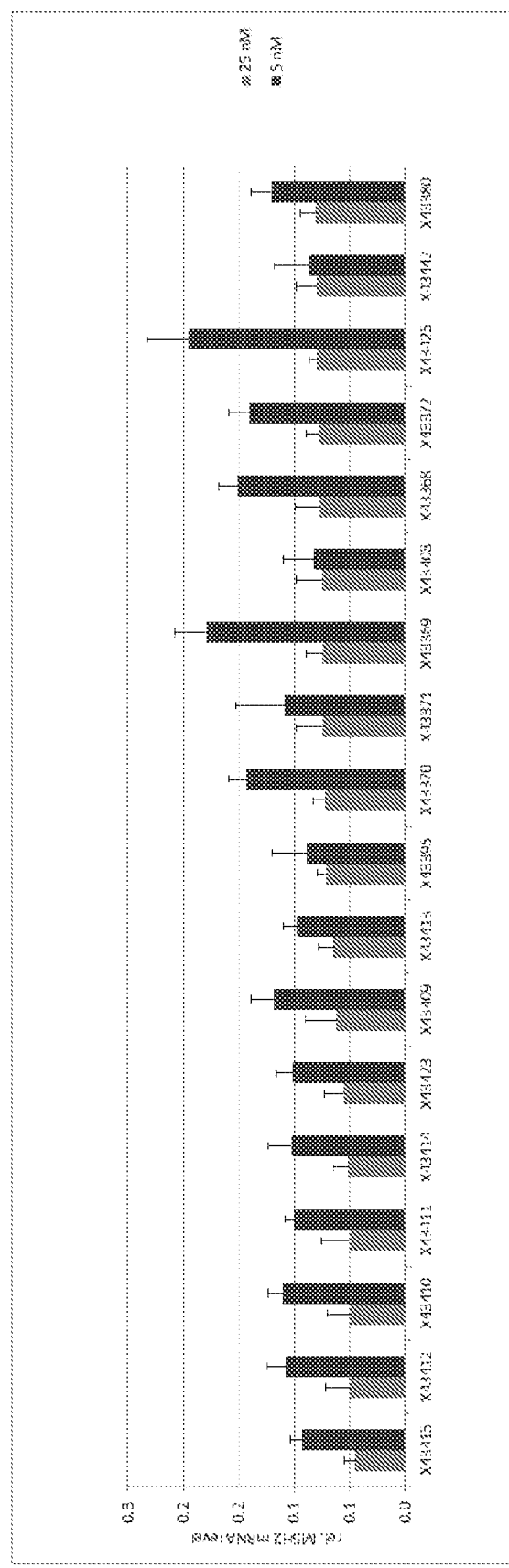
FIG. 5a details impact of various gapmers targeting MSH2 on relative mRNA levels in HELA cells.

The activity of 96 different gapmers, including both LNA and MOE gapmers, targeting the human MSH2 was assessed in a dual dose screen using HeLa cells plated at a density of 15,000 cells/96 wells. The HeLa cells were reverse transfected with lipofectamine 2000 (0.4 µl/well). Doses screened were 5 nM and 25 nM. Impact on MSH2 mRNA was assessed after 24 hrs. MSH2 mRNA levels was normalized to gaph mRNA. Referring to FIGS. 5a, 5b and 7, of the 96 gapmers assessed, 37 reduced MSH2 mRNA to a relative level equal to or less than 0.100 at the 25 nM dose, with 18 (as shown in FIG. 5a) reducing it to below 0.08 at the 25 nM dose. 42 of the 96 gapmers assessed, reduced MSH2 mRNA relative level to between 0.103 and 0.251 at the 25 nM dose. 11 of the 96 gapmers assessed at the 25 nM dose, reduced MSH2 mRNA relative level to between 0.272 and 0.442 at the 25 nM dose. 8 of the 96 gapmers showed some cellular toxicity.

Referring to FIG. 5b, the dose response of candidate gapmers was assessed, with the best ones showing IC50 values in the 2-digit picomolar range.

The disclosure of all patents, publications, including published patent applications, and database entries referenced in this specification are expressly incorporated by reference in their entirety to the same extent as if each such individual patent, publication, and database entry were expressly and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The invention claimed is:

1. A method of increasing tumor mutation burden of a cancer in a subject comprising administering to the subject an effective amount of a gapmer that specifically targets MSH2, wherein the gapmer selected from the group consisting of:
   a. a gapmer type LNA having a gapmer sequence selected from the group consisting of:
      i. AbsTbsAbs(5MdC)s(5MdC)s(5MdC)sdTsdGsdAsdTsdAsdGsdAsGbsTbs CbsGb (SEQ ID NO:31),
      ii. GbsTbsCbsdGsdGsdTsdTsdAsdAsdGsdAsdTs(5MdC)sTbsGbsGbsGb (SEQ ID NO:32),
      iii. AbsTbsCbsdGsdAs(5MdC)sdGsdAsdAsdGsdTsdAsdAsAbsTbsCbsTb (SEQ ID NO:33),
      iv. GbsGbsGbsdAsdAsdTs(5MdC)sdGsdAs(5MdC)sdGsdAsdAsGbsTbsAbsAb(SEQ ID NO:34),
      v. TbsAbsCbs(5MdC)s(5MdC)sdTsdGsdAsdTsdAsdGsdAsdGsTbsCbsGbsGb(SEQ ID NO:35),
      vi. TbsCbsGbsdAs(5MdC)sdGsdAsdAsdGsdTsdAsdAsdAsTbsCbsTbsTb (SEQ ID NO:37),
      vii. AbsAbsGbsdTs(5MdC)sdGsdGsdTsdTsdAsdAsdGsdAsTbsCbsTbsGb (SEQ ID NO:38),
      viii. CbsCbsCbsdTsdGsdAsdTsdAsdGsdAsdGsdTsCbsGbsGbsTb(SEQ ID NO: 39),
      ix. GbsGbsGbsdAsdAsdTs(5MdC)sdGsdAs(5MdC)sdGsAbsAbsGbsTb (SEQ ID NO: 40),
      x. GbsTbsCbsdGsdGsdTsdTsdAsdAsdGsdAsTbsCbsTbsGb (SEQ ID NO: 41),
      xi. AbsTbsCbsdGsdAs(5MdC)sdGsdAsdAsdGsdTs-AbsAbsAbsTb (SEQ ID NO: 42),
      xii. CbsTbsCbsdTsdAsdTsdAs(5MdC)sdTsdGsdAs(5MdC)sdGsAbsAbsCbsCb (SEQ ID NO:43),
      xiii. TbsCbsGbsdAs(5MdC)sdGsdAsdAsdGsdTsdAs-AbsAbsTbsCb (SEQ ID NO: 44),
      xiv. AbsGbsTbs(5MdC)sdGsdGsdTsdTsdAsdAsdGs-AbsTbsCbsTb (SEQ ID NO: 45), and
      xv. GbsTbsAbsdTsdAs(5MdC)sdGsdTs(5MdC)sdAsdTsTbsAbsGbsGb (SEQ ID NO: 48); and
   b. a gapmer type MOE having a gapmer sequence selected from the group consisting of:
      i. GmsGmsCmsCmsAmsdTs(5MdC)sdAsdAs(5MdC)sdTsdGs(5MdC)sdGsdGsAmsCmsAmsUmsUm (SEQ ID NO:36),
      ii. CmsCmsGmsGmsUmsdTsdGsdAsdGsdGsdTs(5MdC)s(5MdC)sdTsdGsAmsUmsAmsAmsAm (SEQ ID NO:46), and
      iii. AmsAmsAmsCmsUmsdTs(5MdC)sdTsdTsdGsdGs(5MdC)sdAsdAsdGsU msCmsGmsGmsUm (SEQ ID NO:47);
wherein dN is a DNA residue, Nb is a LNA residue, Nm is a 2'-MOE residue and s is phosphorothioate.

2. A method of treating cancer in a subject comprising administering to the subject an effective amount a gapmer that specifically targets MSH2 in combination with a second therapeutic, wherein the gapmer selected from the group consisting of:
   a. a gapmer type LNA having a gapmer sequence selected from the group consisting of:
      i. AbsTbsAbs(5MdC)s(5MdC)s(5MdC)sdTsdGsdAsdTsdAsdGsdAsGbsTbs CbsGb (SEQ ID NO:31),
      ii. GbsTbsCbsdGsdGsdTsdTsdAsdAsdGsdAsdTs(5MdC)sTbsGbsGbsGb (SEQ ID NO:32),
      iii. AbsTbsCbsdGsdAs(5MdC)sdGsdAsdAsdGsdTsdAsdAsAbsTbsCbsTb (SEQ ID NO:33),
      iv. GbsGbsGbsdAsdAsdTs(5MdC)sdGsdAs(5MdC)sdGsdAsdAsGbsTbsAbs Ab (SEQ ID NO:34),
      v. TbsAbsCbs(5MdC)s(5MdC)sdTsdGsdAsdTsdAsdGsdAsdGsTbsCbsGbsG b (SEQ ID NO:35),
      vi. TbsCbsGbsdAs(5MdC)sdGsdAsdAsdGsdTsdAsdAsdAsTbsCbsTbsTb (SEQ ID NO:37),
      vii. AbsAbsGbsdTs(5MdC)sdGsdGsdTsdTsdAsdAsdGsdAsTbsCbsTbsGb (SEQ ID NO:38),
      viii. CbsCbsCbsdTsdGsdAsdTsdAsdGsdAsdGsdTsCbsGbsGbsTb (SEQ ID NO: 39),
      ix. GbsGbsGbsdAsdAsdTs(5MdC)sdGsdAs(5MdC)sdGsAbsAbsGbsTb (SEQ ID NO: 40),
      x. GbsTbsCbsdGsdGsdTsdTsdAsdAsdGsdAsTbsCbsTbsGb (SEQ ID NO: 41),
      xi. AbsTbsCbsdGsdAs(5MdC)sdGsdAsdAsdGsdTs-AbsAbsAbsTb (SEQ ID NO: 42),
      xii. CbsTbsCbsdTsdAsdTsdAs(5MdC)sdTsdGsdAs(5MdC)sdGsAbsAbsCbsC b (SEQ ID NO:43),
      xiii. TbsCbsGbsdAs(5MdC)sdGsdAsdAsdGsdTsdAs-AbsAbsTbsCb (SEQ ID NO: 44),
      xiv. AbsGbsTbs (5MdC)sdGsdGsdTsdTsdAsdAsdGs-AbsTbsCbsTb (SEQ ID NO: 45), and
      xv. GbsTbsAbsdTsdAs(5MdC)sdGsdTs(5MdC)sdAsdTsTbsAbsGbsGb (SEQ ID NO: 48); and
   b. a gapmer type MOE having a gapmer sequence selected from the group consisting of:
      i. GmsGmsCmsCmsAmsdTs(5MdC)sdAsdAs(5MdC)sdTsdGs (5MdC)sdGs dGsAmsCmsAmsUmsUm (SEQ ID NO:36),
      ii. CmsCmsGmsGmsUmsdTsdGsdAsdGsdGsdTs(5MdC)s(5MdC)sdTsdGsA msUmsAmsAmsAm (SEQ ID NO:46), and
      iii. AmsAmsAmsCmsUmsdTs(5MdC)sdTsdTsdGsdGs(5MdC)sdAsdAsdGsU msCmsGmsGmsUm (SEQ ID NO:47);
wherein dN is a DNA residue, Nb is a LNA residue, Nm is a 2'-MOE residue and s is phosphorothioate; and
wherein the second therapeutic is an immunotherapeutic.

3. The method of claim 2, wherein the immunotherapeutic is an agent or combination of agents that enhance the immune system to recognize and kill tumor cells.

4. The method of claim 2, wherein immunotherapeutic is an immune checkpoint inhibitor.

5. The method of claim 4, wherein the immune checkpoint inhibitor is an anti-CTLA-4 therapeutic, anti-PD-1 inhibitor or a PD-L1 inhibitor.

6. A method to increase a visibility of a cancer to the immune system in a subject comprising administering to the subject an effective amount of a gapmer that specifically targets MSH2, wherein the gapmer selected from the group consisting of:
   i. AbsTbsAbs(5MdC)s(5MdC)s(5MdC)sdTsdGsdAsdTsdAsdGsdAsGbsTbs CbsGb (SEQ ID NO:31),
   ii. GbsTbsCbsdGsdGsdTsdTsdAsdAsdGsdAsdTs(5MdC)sTbsGbsGbsGb (SEQ ID NO:32),
   iii. AbsTbsCbsdGsdAs(5MdC)sdGsdAsdAsdGsdTsdAsdAsAbsTbsCbsTb (SEQ ID NO:33),
   iv. GbsGbsGbsdAsdAsdTs(5MdC)sdGsdAs(5MdC)sdGsdAsdAsGbsTbsAbs Ab (SEQ ID NO:34),
   v. TbsAbsCbs(5MdC)s(5MdC)sdTsdGsdAsdTsdAsdGsdAsdGsTbsCbsGbsG b (SEQ ID NO:35),
   vi. TbsCbsGbsdAs(5MdC)sdGsdAsdAsdGsdTsdAsdAsdAsTbsCbsTbsTb (SEQ ID NO:37),
   vii. AbsAbsGbsdTs(5MdC)sdGsdGsdTsdTsdAsdAsdGsdAsTbsCbsTbsGb (SEQ ID NO:38),
   viii. CbsCbsCbsdTsdGsdAsdTsdAsdGsdAsdGsdTsCbsGbsGbsTb (SEQ ID NO: 39),
   ix. GbsGbsGbsdAsdAsdTs(5MdC)sdGsdAs(5MdC)sdGsAbsAbsGbsTb (SEQ ID NO: 40), x. GbsTbsCbsdGsdGsdTsdTsdAsdAsdGsdAsTbsCbsTbsGb (SEQ ID NO: 41),
xi. AbsTbsCbsdGsdAs(5MdC)sdGsdAsdAsdGsdTsAbsAbsAbsTb (SEQ ID NO: 42),
xii. CbsTbsCbsdTsdAsdTsdAs(5MdC)sdTsdGsdAs(5MdC)sdGsAbsAbsCbsC b (SEQ ID NO:43),
xiii. TbsCbsGbsdAs(5MdC)sdGsdAsdAsdGsdTsdAsAbsAbsTbsCb (SEQ ID NO: 44),
xiv. AbsGbsTbs (5MdC)sdGsdGsdTsdTsdAsdAsdGsAbsTbsCbsTb (SEQ ID NO: 45), and
xv. GbsTbsAbsdTsdAs(5MdC)sdGsdTs(5MdC)sdAsdTsTbsAbsGbsGb (SEQ ID NO: 48); and
c. a gapmer type MOE having a gapmer sequence selected from the group consisting of:
   i. GmsGmsCmsCmsAmsdTs(5MdC)sdAsdAs(5MdC)sdTsdGs (5MdC)sdGs dGsAmsCmsAmsUmsUm (SEQ ID NO:36),
   ii. CmsCmsGmsGmsUmsdTsdGsdAsdGsdGsdTs(5MdC)s(5MdC)sdTsdGsA msUmsAmsAmsAm (SEQ ID NO:46), and
   iii. AmsAmsAmsCmsUmsdTs(5MdC)sdTsdTsdGsdGs(5MdC)sdAsdAsdGsU msCmsGmsGmsUm (SEQ ID NO:47);

wherein dN is a DNA residue, Nb is a LNA residue, Nm is a 2'-MOE residue and s is phosphorothioate.

7. The method of claim 6, wherein the method increases neoantigens.

8. The method of claim 4, wherein the checkpoint inhibitor is durvalumab, tremelimumab, pembrolizumab, nivolumab, ipilumumab or atezolizumab, or combinations thereof.

* * * * *